US011684610B2

(12) United States Patent
Kweon et al.

(10) Patent No.: US 11,684,610 B2
(45) Date of Patent: Jun. 27, 2023

(54) PHARMACEUTICAL COMPOSITION INCLUDING 1,2-NAPHTHOQUINONE DERIVATIVE COMPOUND FOR PREVENTION OR TREATMENT OF SOLID CANCERS OR BLOOD CANCERS

(71) Applicant: YUNGJIN PHARM. CO., LTD., Seoul (KR)

(72) Inventors: Ki Ryang Kweon, Daejeon (KR); Jun Young Heo, Jeonju-si (KR); Min Ho Shong, Daejeon (KR); Jeong Su Han, Daejeon (KR); Min Jeong Ryu, Daejeon (KR)

(73) Assignee: YUNGJIN PHARM. CO., LTD., Seoul (KR)

( * ) Notice: Subject to any disclaimer, the term of this patent is extended or adjusted under 35 U.S.C. 154(b) by 3 days.

(21) Appl. No.: 17/045,882

(22) PCT Filed: Apr. 4, 2019

(86) PCT No.: PCT/KR2019/004002
§ 371 (c)(1),
(2) Date: Oct. 7, 2020

(87) PCT Pub. No.: WO2019/198977
PCT Pub. Date: Oct. 17, 2019

(65) Prior Publication Data
US 2021/0137893 A1 May 13, 2021

(30) Foreign Application Priority Data

Apr. 9, 2018 (KR) .................. 10-2018-0040884
Apr. 9, 2018 (KR) .................. 10-2018-0040895
Apr. 9, 2018 (KR) .................. 10-2018-0040913

(51) Int. Cl.
*A61K 31/4184* (2006.01)
*A61P 35/02* (2006.01)
*A61P 35/00* (2006.01)
*A61K 31/4192* (2006.01)
*A61K 31/423* (2006.01)
*A61K 31/428* (2006.01)
*A61K 31/4745* (2006.01)
*C07D 263/60* (2006.01)
*C07D 401/04* (2006.01)
*C07D 405/04* (2006.01)
*C07D 413/04* (2006.01)
*C07D 417/04* (2006.01)

(52) U.S. Cl.
CPC ...... *A61K 31/4184* (2013.01); *A61K 31/4192* (2013.01); *A61K 31/423* (2013.01); *A61K 31/428* (2013.01); *A61K 31/4745* (2013.01); *A61P 35/00* (2018.01); *A61P 35/02* (2018.01); *C07D 263/60* (2013.01); *C07D 401/04* (2013.01); *C07D 405/04* (2013.01); *C07D 413/04* (2013.01); *C07D 417/04* (2013.01)

(58) Field of Classification Search
CPC .... A61K 31/4184; A61P 35/00; C07D 401/04
See application file for complete search history.

(56) References Cited

FOREIGN PATENT DOCUMENTS

| JP | 2016-516775 | 6/2016 |
| JP | 2017-502976 | 1/2017 |
| KR | 10-1501612 | 3/2015 |
| KR | 10-2015-0080423 | 7/2015 |
| KR | 10-2015-0080425 | 7/2015 |
| KR | 10-2015-0080426 | 7/2015 |
| KR | 10-2016-0116211 | 10/2016 |
| KR | 10-2016-0116296 | 10/2016 |
| WO | 2016-159577 | 10/2016 |
| WO | 2017-035982 | 3/2017 |
| WO | 2018-005279 | 1/2018 |

OTHER PUBLICATIONS

EPO, Search Report of EP 19785157.9 dated Dec. 15, 2021.
KIPO, PCT Search Report & Written Opinion of PCT/KR2019/004002 dated Jul. 16, 2019.
Xiang Li et al., "Novel naphtho[2,1-d]oxazole-4,5-diones as NQO1 substrates with improved aqueous solubility Design, synthesis, and in vivo antitumor evaluation", Bioorganic & Medicinal Chemistry, Jan. 16, 2016, 24, 5, 1006-1013. http://dx.doi.org/10.1016/j.bmc.2016.01.024.
Huidan Huang et al., "Identification of ortho-naphthoquinones as anti-AML agents by highly efficient oxidation of phenols", Bioorganic Chemistry, 2019, Jan. 18, 2019, 86, 97-102. https://doi.org/10.1016/j.bioorg.2019.01.025.
KIPO, PCT Search Report & Written Opinion of PCT/KR2019/004001 dated Jul. 16, 2019.
Barry, M. A. et al., "Activation of programmed cell death (apoptosis) by cisplatin, other anticancer drugs, toxins and hyperthermia", Biochem Pharmacol., 40(10), 2353-2362, 1990.
Hickman, J. A., "Apoptosis induced by anticancer drugs", Cancer Metastasis Rev., 11(2), 121-139, 1992.
Fesus, L. et al., "Probing the molecular program of apoptosis by cancer chemopreventive agents", J Cell Biochem Suppl., 22, 151-161, 1995.

(Continued)

Primary Examiner — Kamal A Saeed
(74) Attorney, Agent, or Firm — Lex IP Meister, PLLC

(57) ABSTRACT

The present invention relates to a pharmaceutical composition for the prevention or treatment of solid cancers or blood cancers such as acute leukemia or chronic leukemia, including, as an active ingredient, a 1,2-naphthoquinone derivative compound or a pharmaceutically acceptable salt thereof, wherein the 1,2-naphthoquinone derivative compound has excellent effects in killing cancer cells of various solid cancers, acute leukemia, and chronic leukemia, and thus, can be useful as a pharmaceutical composition for the prevention or treatment of cancer, in particular, solid cancers, acute leukemia, or chronic leukemia.

6 Claims, 6 Drawing Sheets

(56) References Cited

OTHER PUBLICATIONS

Reddy, B. S. et al., "Chemoprevention of colon carcinogenesis by dietary perillyl alcohol", Cancer Res., 57(3), 420-425, 1997.
JPO, Office Action of JP 2020-555342 dated Dec. 20, 2022.

[Fig. 1]
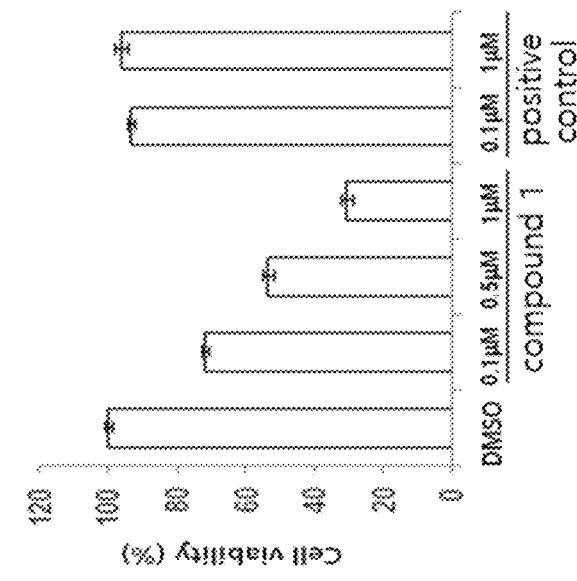
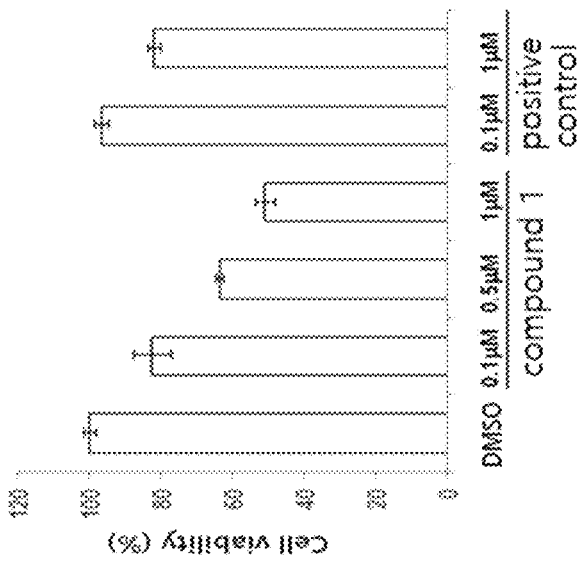

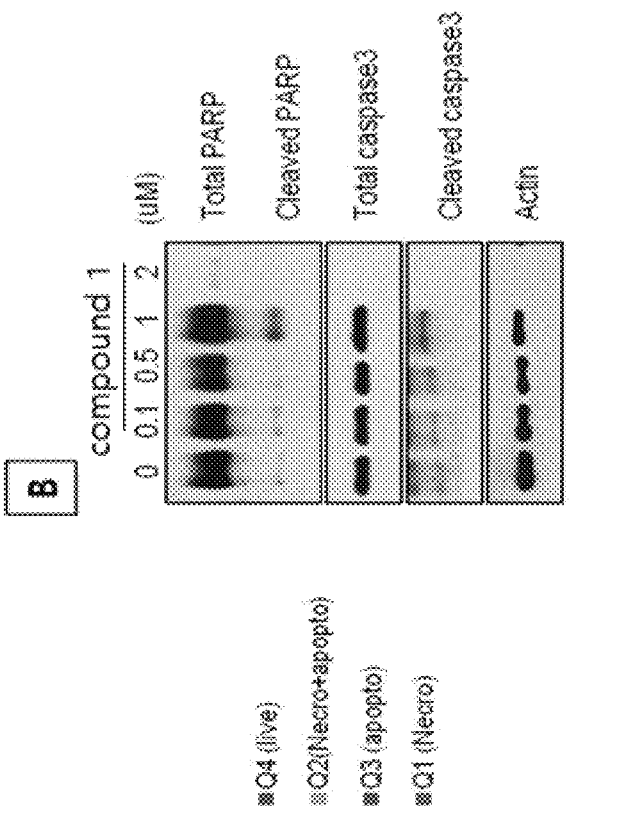
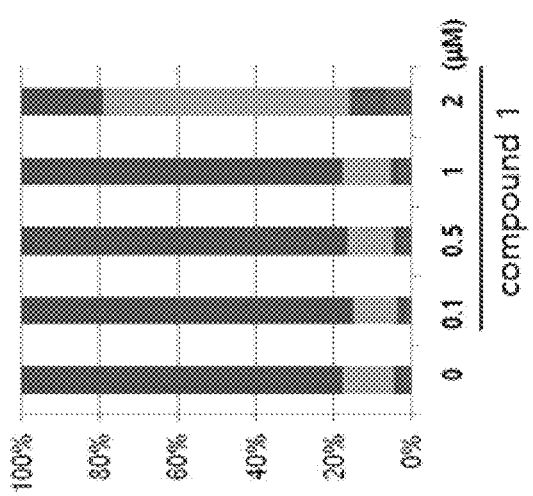
[Fig. 2]

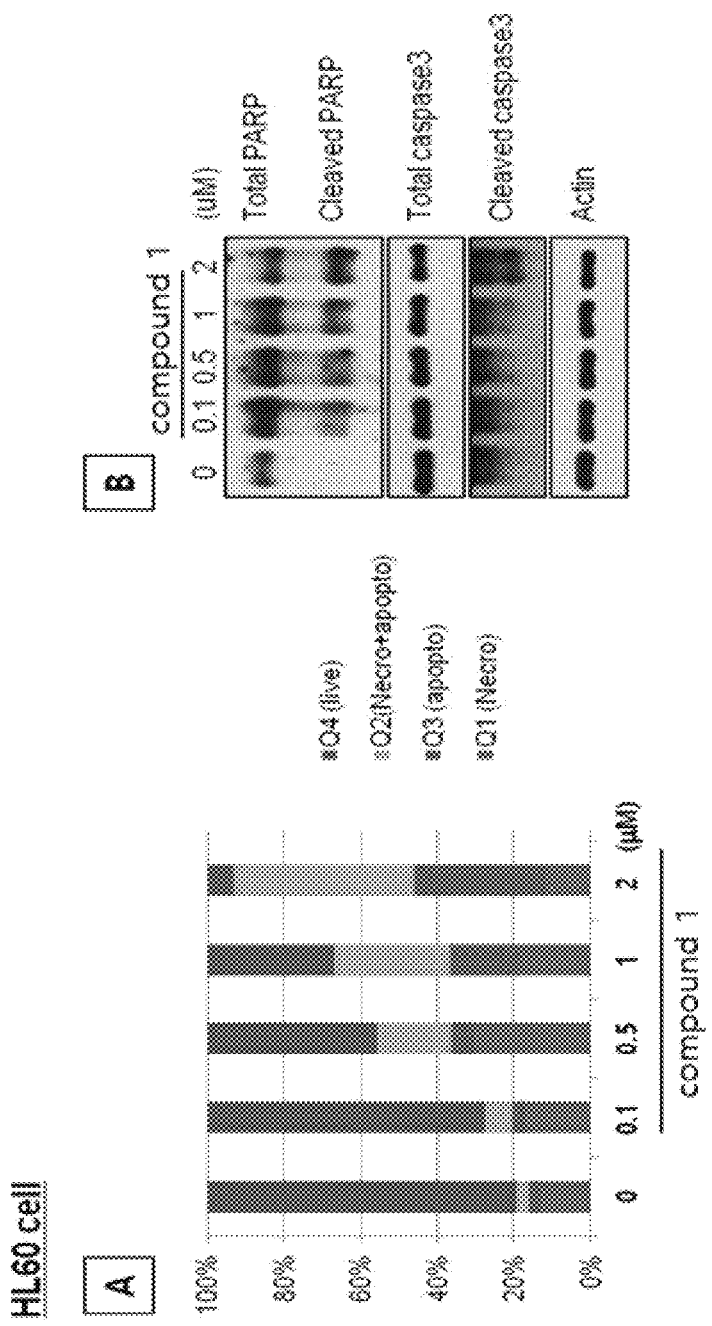

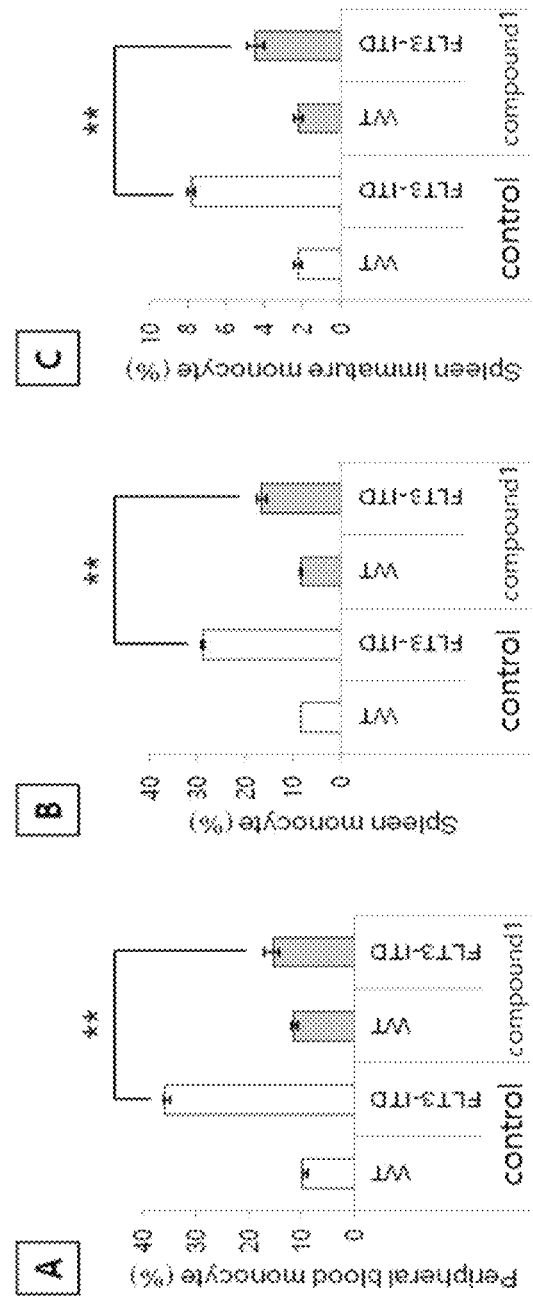

[Fig. 5]
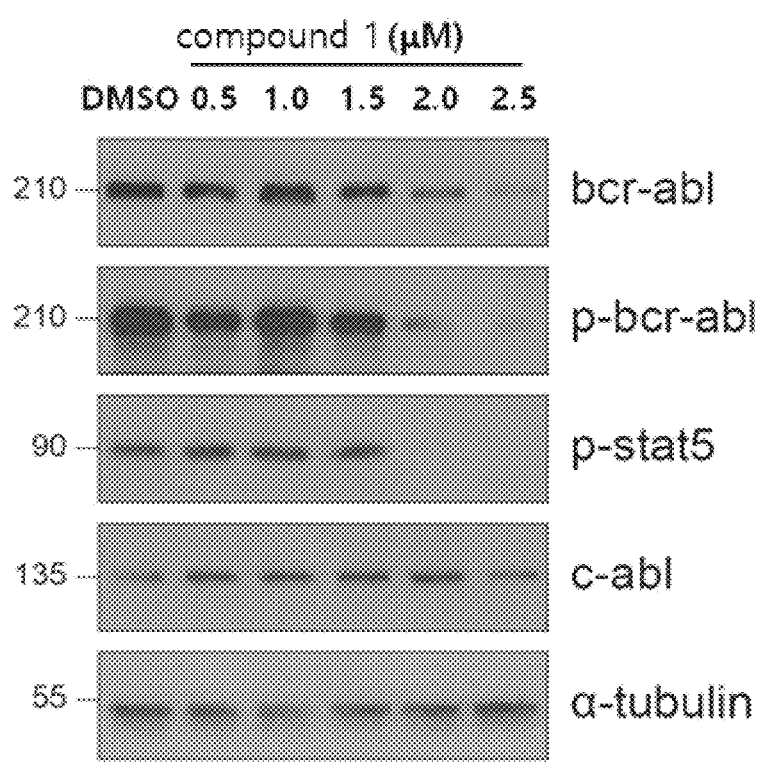

[Fig. 6]
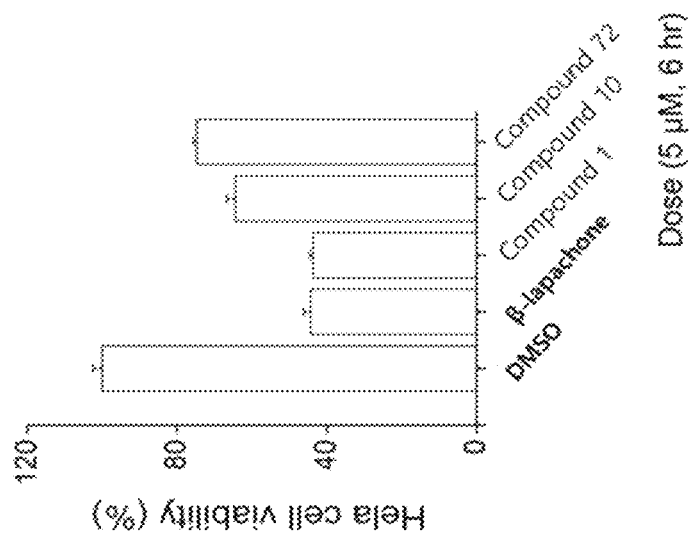
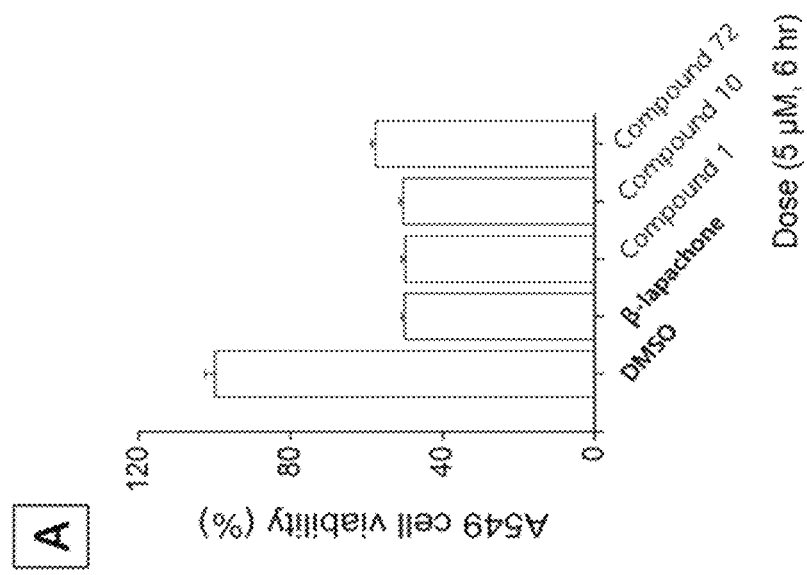

PHARMACEUTICAL COMPOSITION INCLUDING 1,2-NAPHTHOQUINONE DERIVATIVE COMPOUND FOR PREVENTION OR TREATMENT OF SOLID CANCERS OR BLOOD CANCERS

CROSS-REFERENCE TO RELATED APPLICATION(S)

This application claims the benefit of Korean Patent Application Nos. 10-2018-0040913, 10-2018-0040884 and 10-2018-0040895 filed on Apr. 9, 2018 with the Korean Intellectual Property Office, the disclosures of which are incorporated herein by reference in their entirety.

TECHNICAL FIELD

The present invention relates to a pharmaceutical composition for the prevention or treatment of solid cancers or blood cancers such as acute leukemia or chronic leukemia, the pharmaceutical composition including a 1,2-naphthoquinone derivative compound.

BACKGROUND ART

Cells, which are the smallest units constituting the body, divide and grow by the regulatory function of the cells themselves under normal conditions, and when the lifespan is exhausted or the cells are damaged, they die by themselves and maintain the balance of whole numbers. However, when problems occur in the regulatory function of the cells themselves due to various causes, abnormal cells that must die normally become overgrown, and in some cases, it invades surrounding tissues and organs to form a mass (lump) and destroys or deforms an existing structure, and this condition can be defined as cancer.

Cancer is one of the intractable diseases that human beings have to solve, and huge capital has been invested in the development to treat cancer worldwide, and medical technology is also developing innovatively. Nevertheless, deaths from cancer tends to persistently increase. According to the announcement of the National Statistical Office, in the case of cancer patients in Korea, it was reported that about 220,000 new cancer patients have occurred on the basis of 2012. This number has increased about twice as much as the number of new cancer patients that occurred in 2002, and it can be seen that the number of cancer patients is increasing rapidly every year. However, among about 220,000 cancer patients, about 70,000 are dying from cancer, so the development of therapeutic agents for treatment of cancer is urgent.

Currently, therapies for cancer patients relies on surgery, radiation therapy, and chemotherapy (administrating about 40 kinds of cytotoxic anticancer substances showing strong cytotoxity), but most of these therapies are also limited to early-stage cancer patients or specific cancers, so deaths from cancer are still increasing.

On the other hand, leukemia is divided into acute and chronic depending on the degree of differentiation of cells, that is, the rate of deterioration, and is divided into myelogenous and lymphocytic depending on the origin of the cell. Thus, it is classified into acute myeloid leukemia, acute lymphoblastic leukemia, chronic myeloid leukemia, and chronic lymphocytic leukemia.

Acute leukemia is a disease in which abnormal leukocyte progenitor cells or platelet progenitor cells are excessively formed due to bone marrow abnormalities. When myeloid cells proliferate, it is called acute myeloid leukemia (AML), and when lymphoid cells proliferate, it is called acute lymphocytic leukemia (ALL). Because abnormal white blood cells increase and occupy the place where hematopoiesis occurs, normal white blood cells, red blood cells, platelets and the like are not formed, so infection or bleeding easily occurs. If left untreated, they die within a few months. Recently, due to the development of chemotherapy, the viability of acute leukemia in infants has significantly improved, but the viability is still low in adults.

Acute myeloid leukemia is a malignant tumor arising from stem cells of non-lymphoid or myeloid leukocytes made in non-lymphocytic or bone marrow, and is a hematopoietic tumor in which a gene mutation occurs in a hematopoietic mother cell, myeloid progenitor cells stop differentiating at various stages and thus, immature myeloblasts proliferate into a monoclonal group. It shows bone marrow dysfunction symptoms such as anemia, fever, increased infectivity, and bleeding tendency, and may also show symptoms of organ infiltration with tumor cells such as spleen enlargement and lymphadenopathy.

Acute lymphocytic leukemia is a blood cancer that develops in the lymphocyte lineage cells in the blood and bone marrow, and is known to be caused by mutations in several genes involved in the process of proliferation, differentiation, maturation and destruction of lymphocyte lineage cells. The cause of the genetic mutation is currently not clearly identified, but it is estimated that genetic predisposition, viruses, multiple carcinogens, and ionizing radiation are involved as in other cancers. Symptoms observed in acute lymphocytic leukemia are symptoms occurring while abnormal leukemia cells impair the process by which normal blood cells are formed, or while abnormal leukemia cells invade organs such as the lymph nodes, spleen, liver, brain, and spinal cord, similarly to other leukemias.

On the other hand, chronic myelogenous leukemia is caused by a philadelphia chromosome, resulting from a transition phenomenon in which a certain portion of human chromosome 9 and chromosome 22 is cut and then the two cuttings change and move their positions with each other. It is a disease caused by excessive proliferation of abnormal cells in the bone marrow while clones of the hematopoietic stem cell having philadelphia chromosome expand abnormally. Because this disease accounts for about 25% of all adult leukemias and occurs frequently in the 30s to 50s elderly, it is also called adult leukemia, but it can occur in all age groups and also occurs even in children or adolescents.

The Philadelphia chromosome causes fusion between ABL gene on chromosome 9 and BCR gene on chromosome 22 due to chromosome transition. The BCR-ABL fusion gene allows the production of a BCR-ABL fusion protein with abnormal tyrosine kinase activity. Activation of abnormal tyrosine kinase enzyme causes abnormal amplification of malignant cells, and thereby blood cancer occurs.

Gleevec® (imatinib) is a drug that competitively binds to the adenosine triphosphate-binding site (ATP) in the BCR-ABL fusion protein and inhibits the enzymatic activity of the protein. However, in some patients, mutations of the BCR-ABL gene lead to resistance to Gleevec and the disease get worse. As a patient group with the limits and resistance of Greeveck has emerged, second-generation (nilotinib) and third-generation (dasatinib) tyrosine kinase inhibitors are being developed, but these drugs also have the disadvantage that complete treatment is not achieved, and the possibilty of treatment success in acute patients has increased by about 30%. Accordingly, research for the treatment of chronic myelogenous leukemia is continuously needed.

Chronic lymphocytic leukemia is a disease in which lymphocytes, a type of white blood cells, grow and turn into tumors, and accordingly, overgrow in the bone marrow, thereby interfering with the production of normal blood cells. When the number of normal white blood cells decreases, the risk of infection increases, and when the number of red blood cells decreases, anemia occurs, and the number of platelets that act as a hemostatic agent decreases, so that the time for stopping the bleeding also increases. Chronic lymphocytic leukemia is very rare in Korea, but it occurs most frequently in the United States. It often appears in men after the age of 50. The cause of the onset of chronic lymphocytic leukemia has not yet been clarified, and is not related to the environment or occupation, but also to virus or radiation irradiation. However, in the case of direct line families with chronic lymphocytic leukemia, the possibility that will develop chronic lymphocytic leukemia or other lymphoproliferative diseases increases by three times as compared with a general population. When there is a family history, it occurs at about 10 years younger than when it is not so.

Standard methods for treating leukemia include chemotherapy, hematopoietic stem cell transplantation, radiation therapy, and the like. In the case of chemotherapy, a method of using in combination with two or more anticancer agents is usually included. The ideal chemotherapy is that anti-leukemia drugs do not suppress normal hematopoiesis, and should show selective effects only on leukemic cells, without causing other harmful side effects. However, most anti-leukemia drugs can kill leukemia cells in close proximity to the ideal state to some degree, but because it also inhibits normal hematopoiesis and causes other harmful side effects, there is a limit to the treatment of leukemia. In addition, drug-resistant leukemia cells are weak in antitumor effect and may cause side effects, so that sufficient chemotherapy may not be performed.

Hematopoietic stem cell transplantation (HSCT) goes beyond the area of bone marrow transplantation (BMT) that used bone marrow in the past, and at present, it means transplantation using all forms of hematopoietic mother cells present in peripheral blood (PB) and cord blood (CB) as a transplant source. Hematopoietic stem cell transplantation is a treatment method in which cancer cells and the patient's own hematopoietic stem cells are removed using anticancer chemotherapy and radiation therapy in hematopoietic patients, and then new hematopoietic mother cells are transplanted. It is becoming an effective and promising treatment tool in various fields such as refractory autoimmune disease, and solid cancer as well as leukemia, aplastic anemia, malignant lymphoma, represented by leukemia, deviating from the limited concept of early bone marrow transplantation. However, until now, it is a treatment method with a high incidence of complications due to high-dose chemotherapy treatment and graft-versus-host disease that occur after allograft.

Therefore, for effective cancer treatment, it is important to establish and apply a treatment plan suitable for each cancer patient using various methods such as radiotherapy, surgery, and chemotherapy. In addition, it is also an important task given to the industry that develops new therapeutic agents for the treatment of various forms of cancers, such as solid tumors and hematologic cancers.

On the other hand, as a prior literature related to 1,2-naphthoquinone derivative compounds, Korean Unexamined Patent Application Publication Nos. 10-2015-0080423, 10-2015-0080425 and 10-2015-0080426 disclose a 1,2-naphthoquinone derivative and its preparation method, However, these patents relate to a composition for the treatment of metabolic diseases, and they have not disclosed that the 1,2-naphthoquinone derivative compound having the structure of the present invention has a therapeutic effect on solid cancer, acute leukemia, and hematocarcinoma such as chronic leukemia.

PRIOR LITERATURE

Patent Literature (Patent Literature 1) Korean Laid-open Patent Publication No. 10-2015-0080423 (entitled 1,2-naphthoquinone derivative and preparation method thereof, published on Jul. 9, 2015)

(Patent Literature 2) Korean Laid-open Patent Publication No. 10-2015-0080425 (entitled 1,2-naphthoquinone derivative and preparation method thereof, published on Jul. 9, 2015)

(Patent Literature 3) Korean Laid-open Patent Publication No. 10-2015-0080426 (entitled 1,2-naphthoquinone derivative and preparation method thereof, published on Jul. 9, 2015)

DETAILED DESCRIPTION OF THE INVENTION

Technical Problem

It is an object of the present invention to provide a pharmaceutical composition for the prevention or treatment of solid cancers or blood cancers, including a 1,2-naphthoquinone derivative compound.

Technical Solution

The present invention relates to a pharmaceutical composition for the prevention or treatment of solid cancers or blood cancers, including, as an active ingredient, a 1,2-naphthoquinone derivative compound represented by the following Chemical Formula 1 or a pharmaceutically acceptable salt thereof. In a preferred embodiment, the blood cancer is acute leukemia, chronic leukemia, drug-resistant chronic leukemia or refractory acute leukemia.

The present invention relates to a pharmaceutical composition for the prevention or treatment of solid cancers, including, as an active ingredient, a 1,2-naphthoquinone derivative compound represented by the following Chemical Formula 1 or a pharmaceutically acceptable salt thereof.

[Chemical Formula 1]

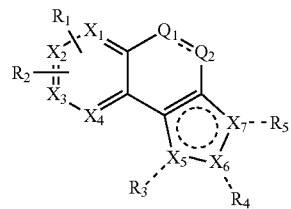

in the Chemical Formula 1, $R_1$ and $R_2$ are each independently hydrogen, halogen, hydroxy, $C_1$-$C_6$ alkoxy, $C_1$-$C_6$ alkyl, $C_4$-$C_{10}$ aryl, $C_4$-$C_{10}$ aryloxy, $C_2$-$C_{10}$ heteroaryl, —$NO_2$, —$NR'_1R'_2$, —$NR'_1(CO)R'_2$), —$NR'_1(C(O)NR'_1R'_2)$, —$CO(O)R'_1$, —$C(O)NR'_1R'_2$, —$CN$, —$SO(O)R'_1$, —$SO(O)NR'_1R'_2$, —$NR'_1(SO$ (O)R'$_2$), —CSNR'$_1$R'$_2$, or R$_1$ and R$_2$ taken together may form a cyclic structure of C$_4$-C$_{10}$ aryl or a cyclic structure of C$_2$-C$_{10}$ heteroaryl, wherein R'$_1$ and R'$_2$ are each independently hydrogen, C$_1$-C$_6$ alkyl, C$_3$-C$_8$ cycloalkyl, or C$_4$-C$_{10}$ aryl, C$_4$-C$_{10}$ aryloxy, C$_1$-C$_8$ heteroaryl, —(CR''$_1$R''$_2$)$_m$—C$_4$-C$_{10}$ aryl, —(CR''$_1$R''$_2$)$_m$—C$_4$-C$_{10}$ heteroaryl or NR''$_1$R''$_2$, the R''$_1$ and R''$_2$ are each independently hydrogen, C$_1$-C$_3$ alkyl, or R''$_1$ and R''$_2$ taken together may form a cyclic structure of C$_4$-C$_{10}$ aryl, R$_3$, R$_4$ and R$_5$ are each independently hydrogen, halogen, hydroxy, C$_1$-C$_6$ alkyl, C$_2$-C$_{10}$ alkene, C$_1$-C$_6$ alkoxy, C$_3$-C$_8$ cycloalkyl, C$_2$-C$_8$ heterocycloalkyl, C$_4$-C$_{10}$ aryl, C$_4$-C$_{10}$ aryloxy, C$_1$-C$_8$ heteroaryl, —(CR'$_5$R'$_6$)$_m$—C$_4$-C$_{10}$ aryl, —(CR'$_5$R'$_6$)$_m$—C$_4$-C$_{10}$ aryloxy, —(CR'$_5$R'$_6$)$_m$—C$_1$-C$_8$ heteroaryl, —(CR'$_5$R'$_6$)$_m$—NR'$_3$R'$_4$, —(CR'$_5$R'$_6$)$_m$—C$_3$-C$_8$ heterocycloalkyl, —(CR'$_5$R'$_6$)$_m$—OR'$_3$, —(CR'$_5$R'$_6$)$_m$(O)COR'$_3$, —CO(O)R'$_3$, —CONR'$_3$R'$_4$, —NR'$_3$R'$_4$, —NR'$_3$(C(O)R'$_4$), —SO(O)R'$_3$, —SO(O)NR'$_3$R'$_4$, —NR'$_3$(SO(O)R'$_4$), —CSNR'$_3$R'$_4$, —CH$_2$A where the compound of Chemical Formula 1 is "A", or -A where the compound of Chemical Formula 1 is "A", wherein the R'$_3$ and R'$_4$ are each independently hydrogen, C$_1$-C$_6$ alkyl, C$_3$-C$_8$ cycloalkyl, C$_4$-C$_{10}$ aryl, —(CR'$_5$R'$_6$)$_m$—C$_4$-C$_{10}$ aryl, —(CR'$_5$R'$_6$)$_m$—C$_4$-C$_{10}$ aryloxy, —(CR'$_5$R'$_6$)$_m$—C$_1$-C$_{10}$ heteroaryl, —CO(O)R''$_3$, or, R'$_3$ and R'$_4$ taken together may form a cyclic structure of C$_2$-C$_{10}$ heterocycloalkyl, or a cyclic structure of C$_1$-C$_{10}$ heteroaryl, the R'$_5$ and R'$_6$ are each independently hydrogen or C$_1$-C$_3$ alkyl, the R''$_3$ is C$_1$-C$_6$ alkyl;

Q$_1$ and Q$_2$ are each independently CO, COR$_6$, or COR$_7$, when Q$_1$ is CO and Q$_2$ is CO, Q$_1$ and Q$_2$ form a single bond, when Q$_1$ is COR$_6$ and Q$_2$ is COR$_7$, Q$_1$ and Q$_2$ form a double bond, the R$_6$ and R$_7$ are each independently hydrogen, C$_1$-C$_{10}$ alkoxy, C$_1$-C$_6$alkyl, C$_4$-C$_{10}$ aryl, C$_4$-C$_{10}$ aryloxy, C$_2$-C$_{10}$ heteroaryl, —CO(O)R'$_7$, —C(O)NR'$_7$R'$_8$, —SO(O)R'$_7$, —SO(O)NR'$_7$R'$_8$, —SO$_3$R'$_7$, —PO$_3$R'$_7$, —CSNR'$_7$R'$_8$, or R$_6$ and R$_7$ taken together may form a cyclic structure of C$_3$-C$_{10}$ heterocyclo alkyl, or a cyclic structure of C$_3$-C$_{10}$ heteroaryl, the R'$_7$ and R'$_8$ are each independently hydrogen, C$_1$-C$_6$ alkyl, C$_3$-C$_8$ cycloalkyl, C$_4$-C$_{10}$ aryl, C$_4$-C$_{10}$ aryloxy, C$_1$-C$_8$ heteroaryl, —(CR''4R''$_5$)m'—C$_4$-C$_{10}$ aryl, the R''$_4$ and R''$_5$ are each independently hydrogen, C$_1$-C$_3$ alkoxy;

Q$_1$ is a cyclic structure of substituted or unsubstituted C$_3$-C$_5$ heterocyclo alkyl, Q$_2$ is CO, or, when Q$_1$ is CO and Q$_2$ is a cyclic structure of substituted or unsubstituted C$_3$-C$_5$ heterocyclo alkyl, Q$_1$ and Q$_2$ form a single bond;

m and m' are each independently an integer of 1 to 4;

the hetero atom is at least one selected from N, O and S;

X$_1$ to X$_4$ are each independently CH or N(R''$_6$), X$_5$ is N, X$_6$ is C, X$_7$ is N, wherein R''$_6$ is hydrogen or C$_1$-C$_3$ alkyl;

in the Chemical Formula, the notation ==== means a single bond or a double bond, the notation ---- means that a single bond or a bond may not be formed, the notation ⌒ means that the cyclic structure including it may or may not be aromatic; and the substituted means being substituted with one or more substituents selected from the group consisting of hydroxy, halogen element, C$_1$-C$_{10}$ alkyl, C$_2$-C$_{10}$ alkenyl, C$_2$-C$_{10}$ alkynyl, C$_1$-C$_{10}$ alkoxy, C$_1$-C$_{10}$ alkoxycarbonyl, C$_3$-C$_8$ cycloalkyl, C$_2$-C$_8$ heterocycloalkyl, C$_4$-C$_{10}$ aryl, and C$_2$-C$_{10}$ heteroaryl.

The term "alkyl" means a linear or branched hydrocarbon group with a single bond, and may include, for example, C$_1$-C$_{10}$ alkyl, specifically C$_1$-C$_6$ alkyl, more specifically methyl, ethyl, propyl, n-butyl, isobutyl, tert-butyl, 1-methylpropyl, and the like.

The term "alkoxy" means an oxygen group to which a linear or branched saturated hydrocarbon with a single bond is bonded, and may include, for example, C$_1$-C$_{10}$ alkoxy, specifically C$_1$-C$_6$ alkoxy, more specifically methoxy, ethoxy, propoxy, n-butoxy, tert-butoxy, 1-methylpropoxy, and the like.

The term "cycloalkyl" means a saturated hydrocarbon ring group with a single bond, and may include, for example, C$_3$-C$_{10}$ cycloalkyl depending on the number of carbon atoms, specifically C$_3$-C$_8$ cycloalkyl, more specifically cyclopropyl, cyclobutyl, cyclopentyl, cyclohexyl, and the like.

The term "heterocycloalkyl" means a saturated hydrocarbon ring group with a single bond including one or more heteroatoms such as N, O, or S in addition to carbon atoms as ring members. Depending on the number and type of heteroatoms contained in the ring, and the number of carbon atoms, for example, the heterocycloalkyl includes C$_2$-C$_8$ heterocycloalkyl, C$_2$-C$_{10}$ heterocycloalkyl, or C$_2$-C$_5$ heterocycloalkyl containing one or more, specifically, one to three heteroatoms selected from the group consisting of N, O and S, more specifically, aziridine, pyrrolidine, pyrrolidinyl, piperidinyl, piperazinyl, morpholinyl, tetrahydrofuranyl or tetrahydropyranyl, and the like.

The term "aryl" means an aromatic substituent containing at least one ring having a shared pi-electron system, and includes monocyclic or fused ring polycyclic (i.e., rings that share pairs of adjacent carbon atoms) groups. For example, depending on the number of carbon atoms contained in the ring, the aryl is specifically C$_4$-C$_{10}$ aryl, more specifically C$_6$-C$_{10}$ aryl, and still more specifically phenyl, naphthyl, and the like.

The term "heteroaryl" means an aromatic cyclic compound containing one or more heteroatoms such as N, O, or S in addition to a carbon atom as a ring member. For example, depending on the number and type of heteroatoms contained in the ring, and the number of carbon atoms, the heteroaryl includes C$_1$-C$_{10}$ heteroaryl, more specifically, C$_1$-C$_8$ heteroaryl, C$_2$-C$_{10}$ heteroaryl, or C$_2$-C$_5$ heteroaryl, containing one or more, specifically one to three heteroatoms selected from the group consisting of N, O, and S.

Examples of the aryl or heteroaryl include phenyl, naphthyl, furanyl, pyranyl, oxazolyl, isoxazolyl, imidazole, pyridyl, pyrazinyl, pyrimidyl, pyridazinyl, oxadiazolyl, thiadiazolyl, tetrazolyl, triazinyl, triazyl, and the like, but are not limited only thereto.

The term "aryloxy" means a group in which any one carbon forming an aromatic substituent is bonded to oxygen. For example, when oxygen is bonded to a phenyl group, it can be expressed as —O—C$_6$H$_5$, —C$_6$H$_4$—O—.

In the present invention, the "substituent" may be at least one, preferably one to three, selected from the group consisting of halo, hydroxy, a cyano group, a nitro group, an unsubstituted or substituted alkyl group, an unsubstituted or substituted alkenyl group, an unsubstituted or substituted alkynyl group, an unsubstituted or substituted alkoxy group, an unsubstituted or substituted alkoxycarbonyl group, an unsubstituted or substituted cycloalkyl group, an unsubstituted or substituted heterocycloalkyl group, an unsubstituted or substituted aryl group, and an unsubstituted and substituted heteroaryl group. Specifically, the substituent may be at least one selected from the group consisting of hydroxy, halo, C$_1$-C$_{10}$ alkyl, C$_2$-C$_{10}$ alkenyl, C$_2$-C$_{10}$ alkynyl, C$_1$-C$_{10}$ alkoxy, $C_1$-$C_{10}$ alkoxycarbonyl, $C_3$-$C_8$ cycloalkyl, $C_2$-$C_8$ heterocycloalkyl, $C_4$-$C_{10}$ aryl, and $C_2$-$C_{10}$ heteroaryl.

In addition, the prodrug containing the 1,2-naphthoquinone derivative compound of the present invention is regarded as one type of compound excluding the case where $Q_1$ is CO and $Q_2$ is CO in the Chemical Formula 1. As an example included in the prodrug, the following compounds and the like correspond thereto.

[Compound 176]
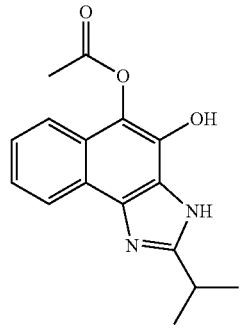

[Compound 179]
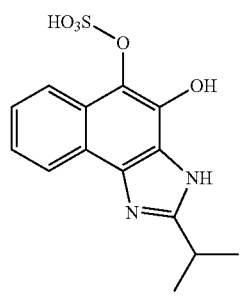

[Compound 181]
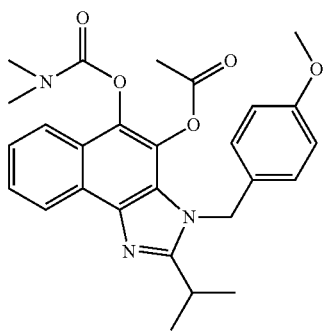

[Compound 185]
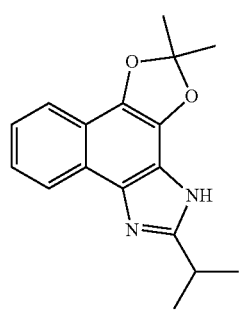

[Compound 190]
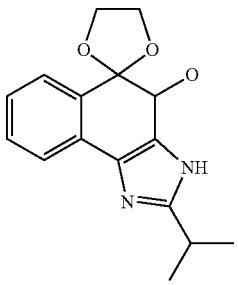

Preferably, it may be a pharmaceutical composition for the treatment of solid cancers or blood cancers, including, as an active ingredient, a 1,2-naphthoquinone derivative compound represented by the Chemical Formula 1 or a pharmaceutically acceptable salt thereof, wherein:

in the Chemical Formula 1, $R_3$ is hydrogen, halogen, hydroxy, $C_1$-$C_6$ alkyl, $C_1$-$C_6$ alkoxy, $C_3$-$C_8$ cycloalkyl, $(CR'_5R'_6)_m$—$C_4$-$C_{10}$ aryl, —$(CR'_5R'_6)_m$—$OR'_3$, —$CO(O)R'_3$, —$CH_2A$ where the compound of Chemical Formula 1 is "A", or -A where the compound of Chemical Formula 1 is "A", wherein $R'_3$ is hydrogen, $C_1$-$C_6$ alkyl, $C_3$-$C_8$ cycloalkyl, $C_4$-$C_{10}$ aryl, —$(CR'R')_m$—$C_4$-$C_{10}$ aryl, —$(CR'R')_m$—$C_4$-$C_{10}$ aryloxy, —$(CR'_5R')_m$—$C_1$-$C_{10}$ heteroaryl, —$CO(O)R''_3$, the $R'_5$ and $R'_6$ are each independently hydrogen, $C_1$-$C_6$ alkyl, the $R''_3$ is $C_1$-$C_6$ alkyl;

$R_4$ is hydrogen, halogen, hydroxy, $C_1$-$C_6$ alkyl, $C_2$-$C_{10}$ alkene, $C_1$-$C_6$ alkoxy, $C_3$-$C_8$ cycloalkyl, $C_2$-$C_8$ heterocycloalkyl, $C_4$-$C_{10}$ aryl, $C_4$-$C_{10}$ aryloxy, $C_1$-$C_8$ heteroaryl, —$(CR'5R'_6)_m$—$C_4$-$C_{10}$ aryl, —$(CR'_5R'_6)_m$—$C_4$-$C_{10}$ aryloxy, —$(CR'_5R'_6)_m$—$C_1$-$C_8$ heteroaryl, —$(CR'_5R'_6)_m$—$NR'_3R'_4$, —$(CR'_5R'_6)_m$—$C_3$-$C_8$ heterocycloalkyl, —$(CR'_5R'_6)_m$—$OR'_3$, —$(CR'_5R'_6)_m(O)COR'_3$, —$CO(O)R'_3$, —$CONR'_3R'_4$, —$NR'_3R'_4$, —$NR'_3(C(O)R'_4)$, -A where the compound of Chemical Formula 1 is "A", wherein $R'_3$ and $R'_4$ are each independently hydrogen, $C_1$-$C_6$ alkyl, $C_3$-$C_8$ cycloalkyl, $C_4$-$C_{10}$ aryl, —$(CR'_5R'_6)_m$—$C_4$-$C_{10}$ aryl, —$(CR'_5R'_6)_m$—$C_4$-$C_{10}$ aryloxy, —$(CR'_5R'_6)_m$—$C_1$-$C_{10}$ heteroaryl, —$CO(O)R''_3$, or $R'_3$ and $R'_4$ taken together may form a cyclic structure of $C_2$-$C_{10}$ heterocycloalkyl, or a cyclic structure of $C_1$-$C_{10}$ heteroaryl, the $R'_5$ and $R'_6$ are each independently hydrogen or $C_1$-$C_3$ alkyl, the $R''_3$ is $C_1$-$C_6$ alkyl;

$R_5$ is hydrogen, halogen, hydroxy, $C_1$-$C_6$ alkyl, $C_2$-$C_{10}$ alkene, $C_1$-$C_6$ alkoxy, $C_3$-$C_8$ cycloalkyl, $C_2$-$C_8$ heterocycloalkyl, $C_4$-$C_{10}$ aryl, $C_4$-$C_{10}$ aryloxy, $C_1$-$C_8$ heteroaryl, —$(CR'5R'_6)_m$—$C_4$-$C_{10}$ aryl, —$(CR'5R'_6)_m$—$C_4$-$C_{10}$ aryloxy, —$(CR'_5R'_6)_m$—$C_1$-$C_8$ heteroaryl, —$(CR'_5R'_6)_m$—$NR'_3R'_4$, —$(CR'_5R'_6)_m$—$C_3$-$C_8$ heterocycloalkyl, —$(CR'_5R'_6)_m$—$OR'_3$, —$(CR'_5R'_6)_m(O)COR'_3$, —$CO(O)R'_3$, —$CONR'_3R'_4$, —$NR'_3R'_4$, —$NR'_3(C(O)R'_4)$, —$CH_2A$ where the compound of Chemical Formula 1 is "A", wherein $R'_3$ and $R'_4$ are each independently hydrogen, $C_1$-$C_6$ alkyl, $C_3$-$C_8$ cycloalkyl, $C_4$-$C_{10}$ aryl, —$(CR'_5R'_6)_m$—$C_4$-$C_{10}$ aryl, —$(CR'_5R'_6)_m$—$C_4$-$C_{10}$ aryloxy, —$(CR'_5R'_6)_m$—$C_1$-$C_{10}$ heteroaryl, —$CO(O)R''_3$, or $R'_3$ and $R'_4$ taken together may form a cyclic structure of $C_2$-$C_{10}$ heterocycloalkyl, or a cyclic structure of $C_1$-$C_{10}$ heteroaryl, the $R'_5$ and $R'_6$ are each independently hydrogen or $C_1$-$C_3$ alkyl, and the $R''_3$ is $C_1$-$C_6$ alkyl;

Further, a more specific example of the compound of the Chemical Formula 1 is as follows.

Compound 1
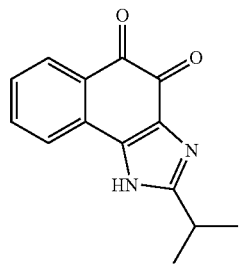
Compound 2
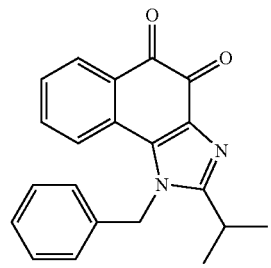
Compound 3
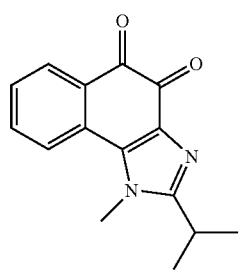
Compound 4
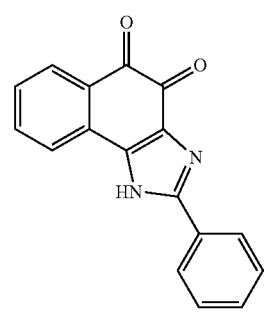
Compound 5
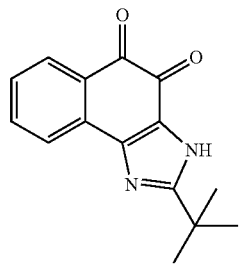
Compound 6
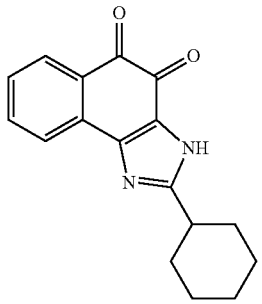
Compound 7
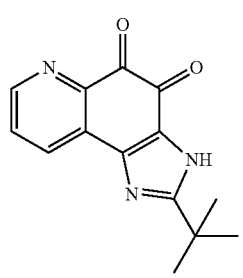
Compound 8
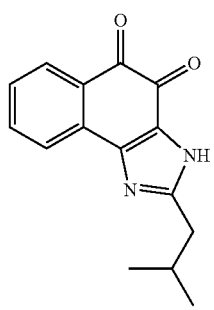
Compound 9
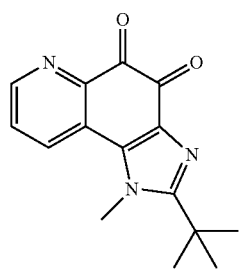
Compound 10
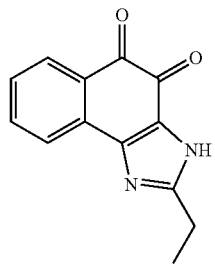

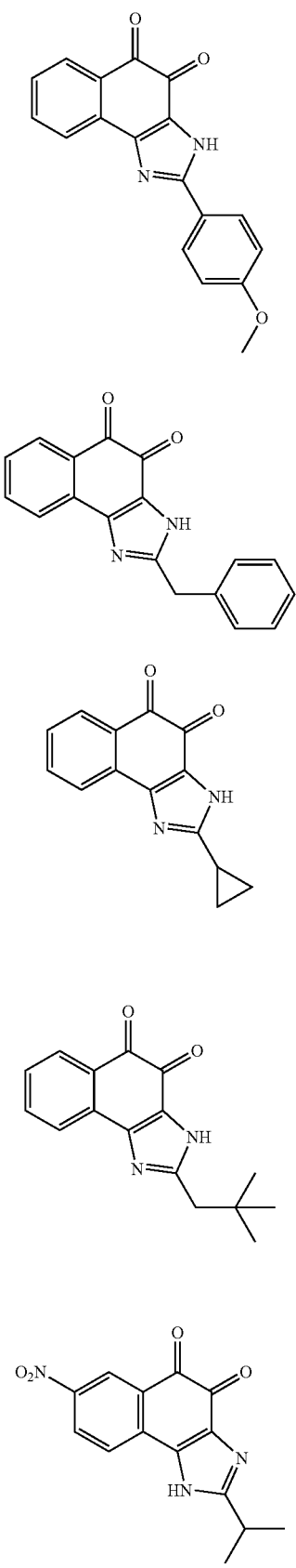
Compound 11
Compound 12
Compound 13
Compound 14
Compound 15
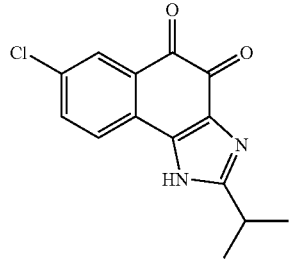
Compound 16
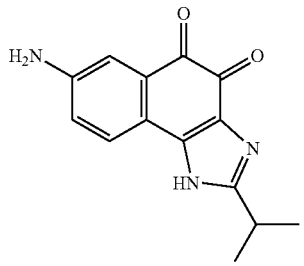
Compound 17
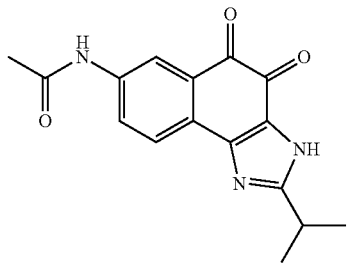
Compound 18
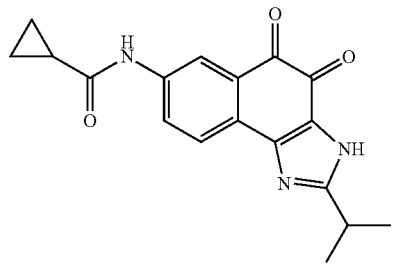
Compound 19
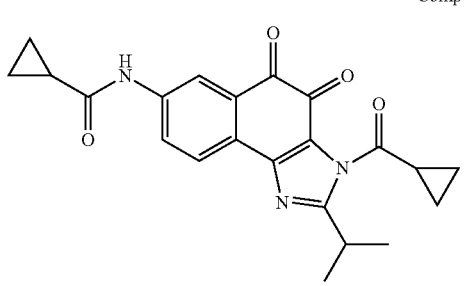
Compound 20
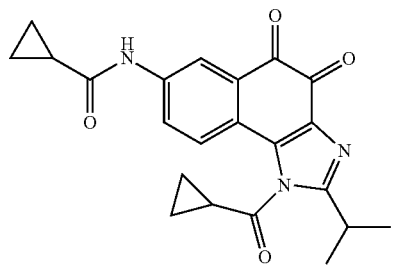
Compound 21

Compound 22
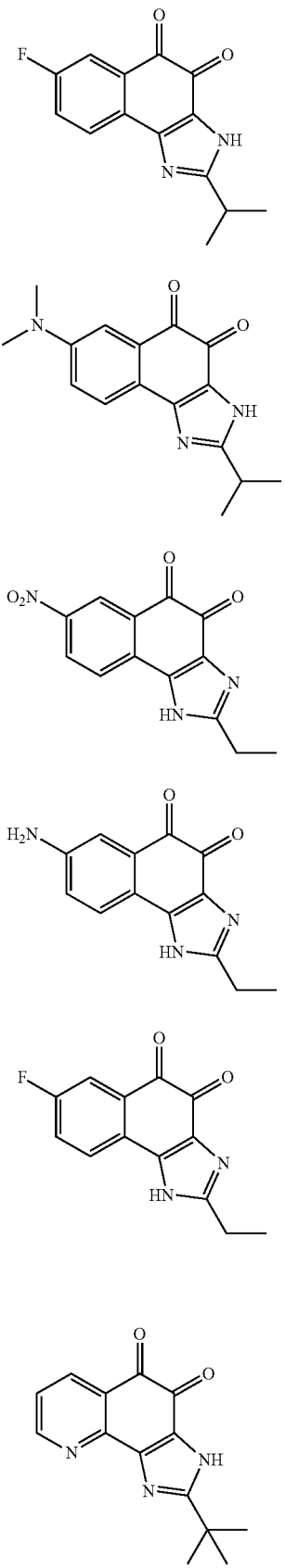
Compound 23
Compound 24
Compound 25
Compound 26
Compound 27
Compound 28
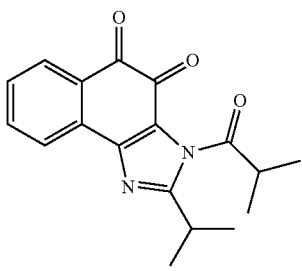
Compound 29
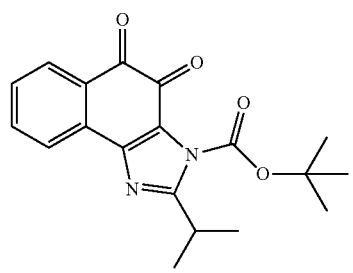
Compound 30
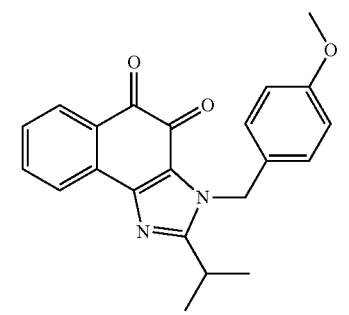
Compound 31
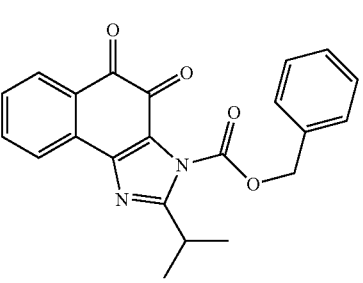
Compound 32
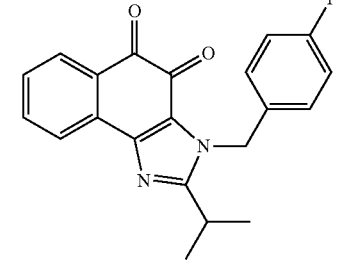

Compound 33
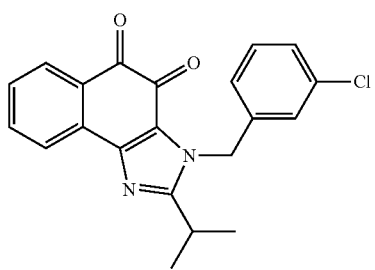
Compound 34
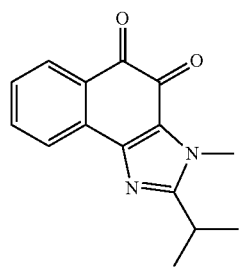
Compound 35
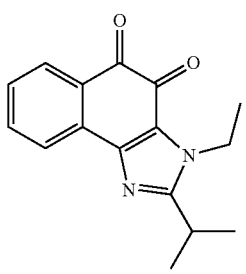
Compound 36
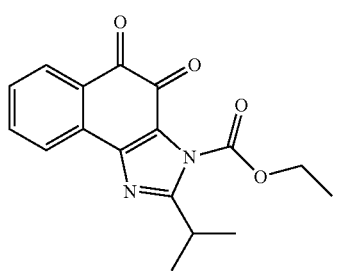
Compound 37
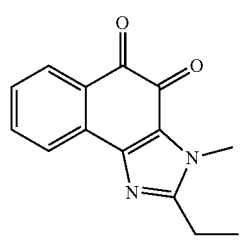
Compound 38
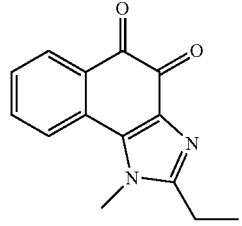
Compound 39
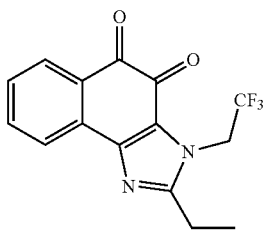
Compound 40
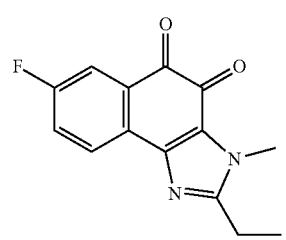
Compound 41
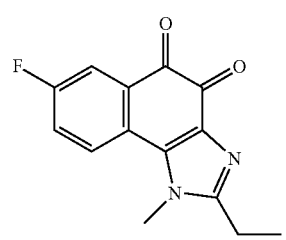
Compound 42
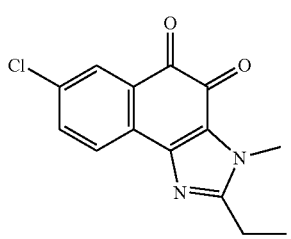
Compound 43
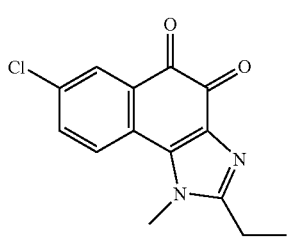
Compound 44
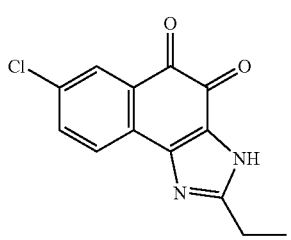

Compound 45
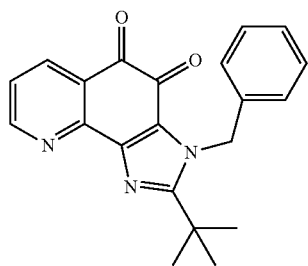
Compound 46
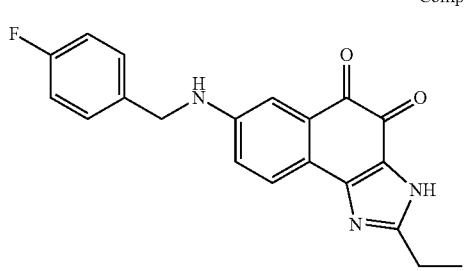
Compound 47
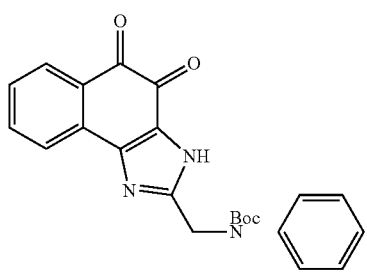
Compound 48
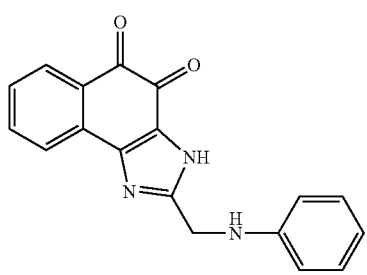
Compound 49
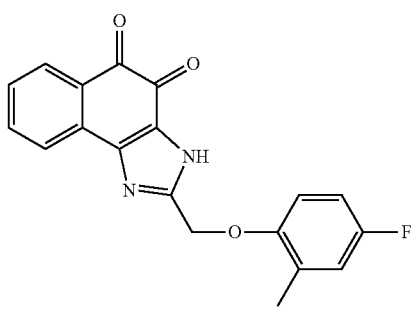
Compound 50
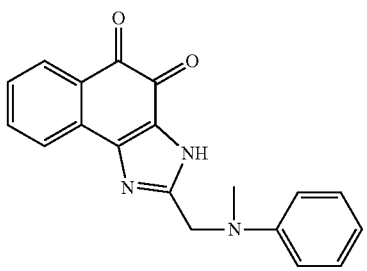
Compound 51
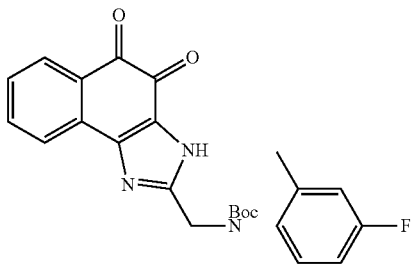
Compound 52
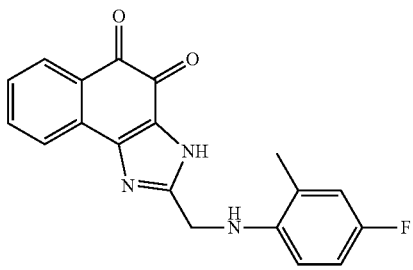
Compound 53
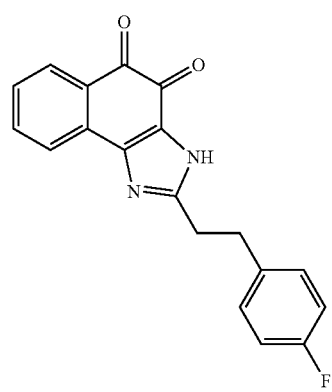
Compound 54
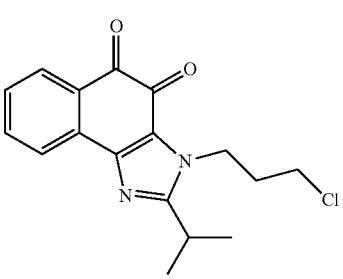

Compound 55
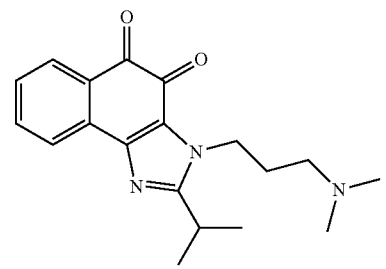
Compound 56
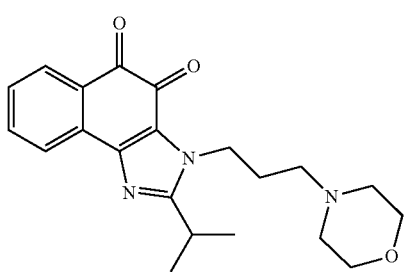
Compound 57
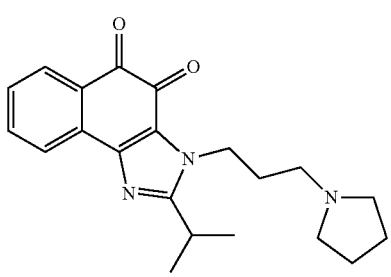
Compound 58
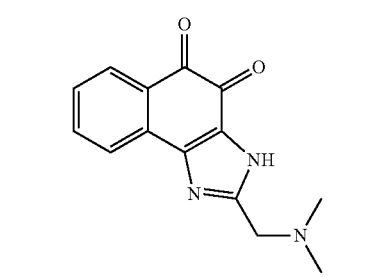
Compound 59
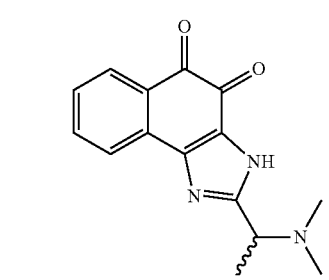
Compound 60
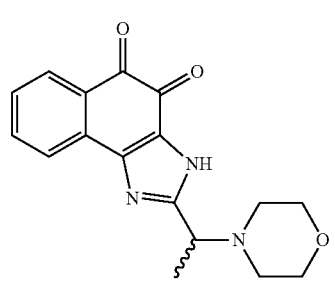
Compound 61
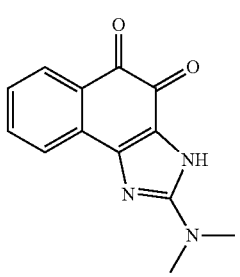
Compound 62
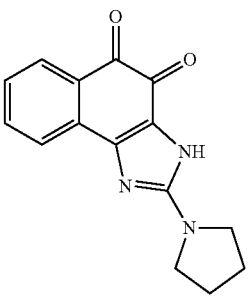
Compound 63
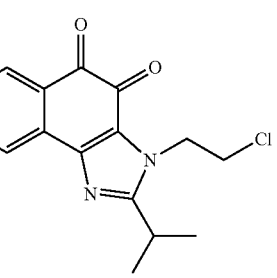
Compound 64
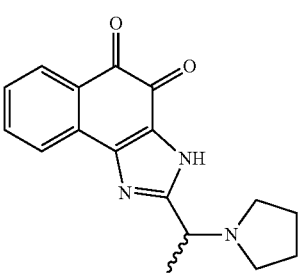
Compound 65
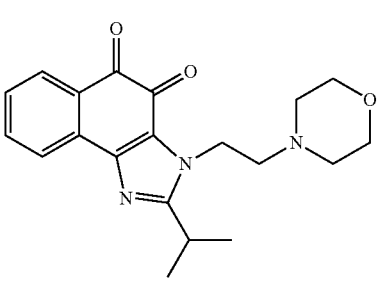

Compound 66
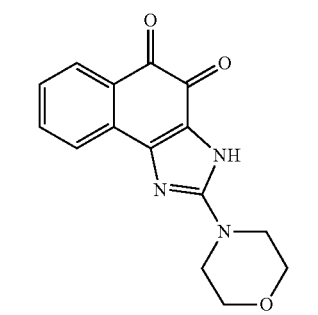
Compound 67
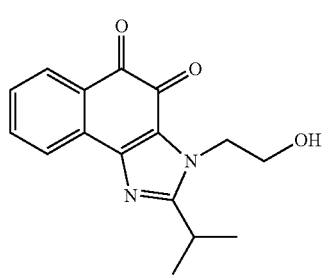
Compound 68
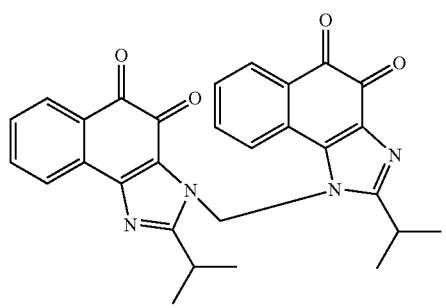
Compound 69
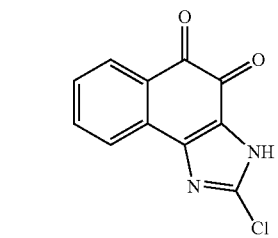
Compound 70
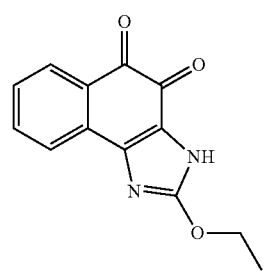
Compound 71
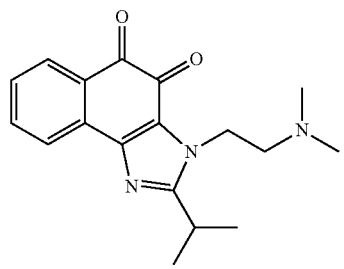
Compound 72
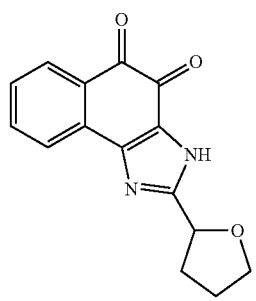
Compound 73
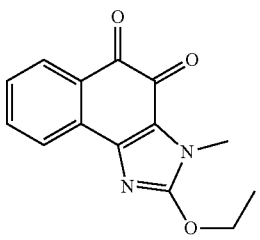
Compound 74
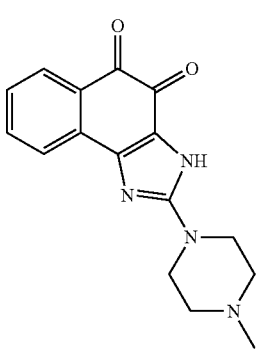
Compound 75
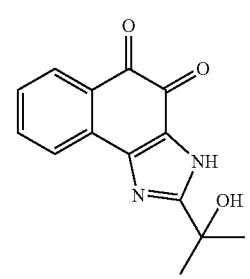

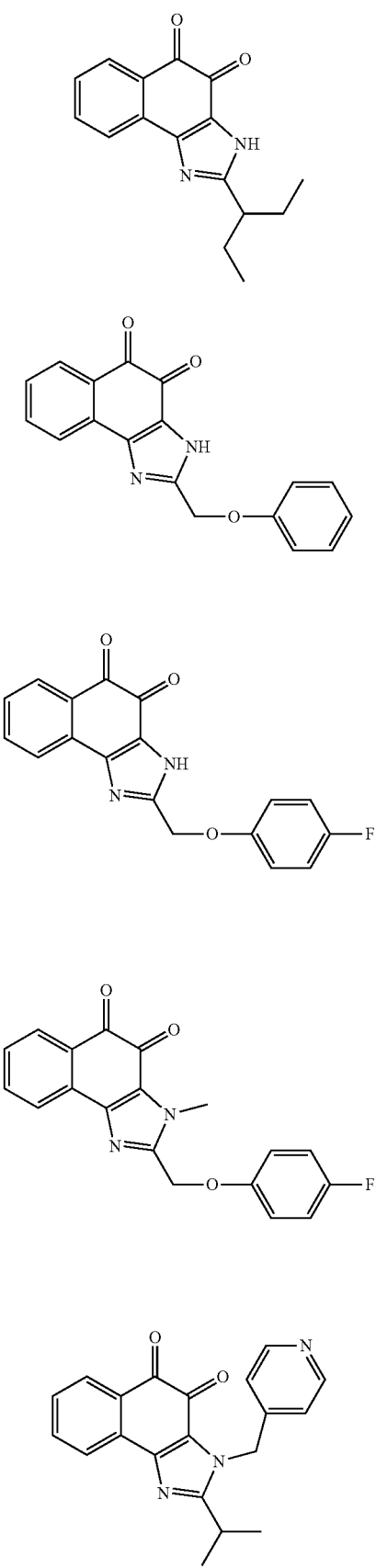
Compound 76
Compound 77
Compound 78
Compound 79
Compound 80
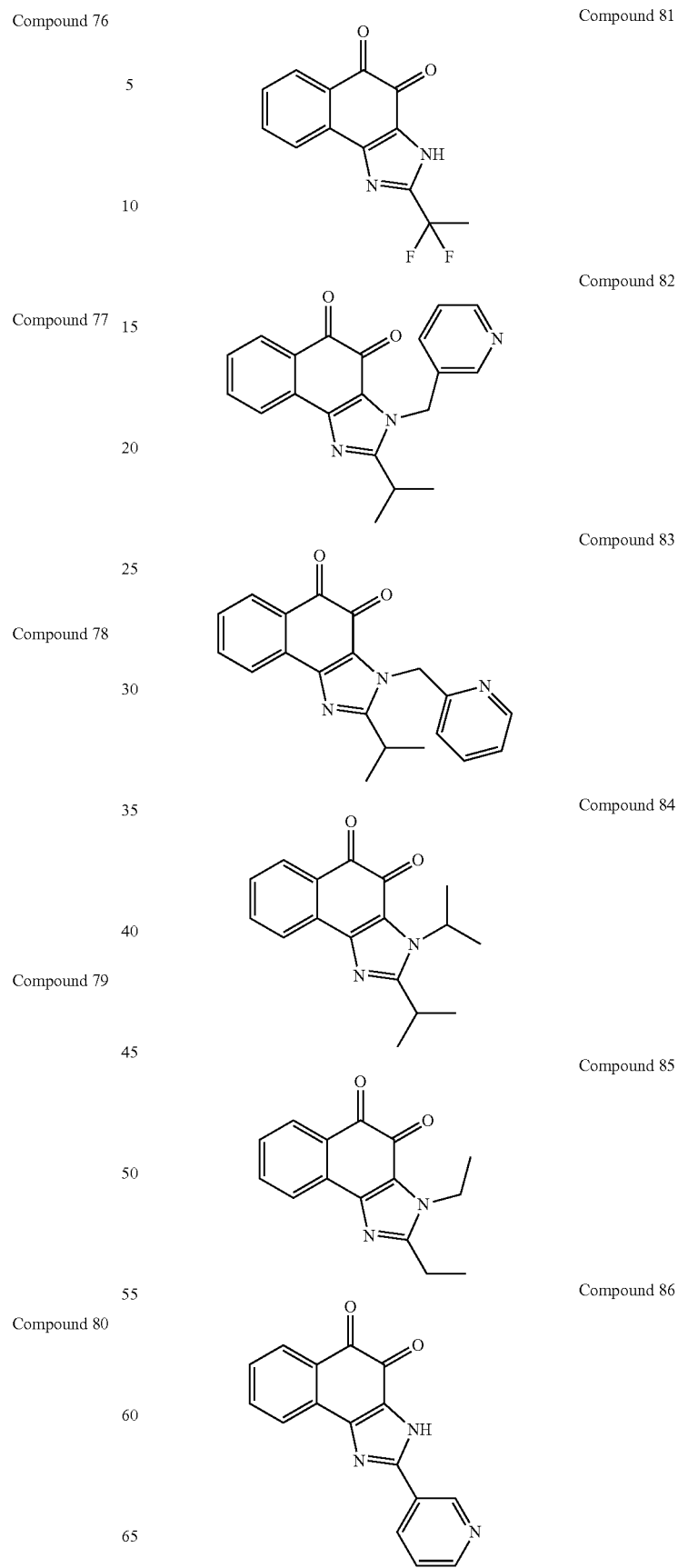
Compound 81
Compound 82
Compound 83
Compound 84
Compound 85
Compound 86

Compound 87
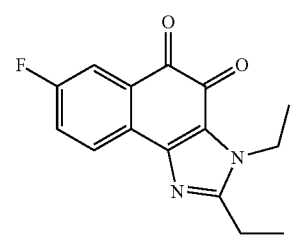
Compound 88
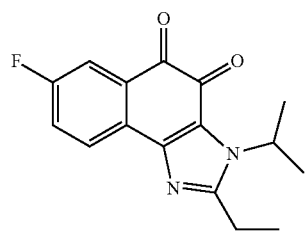
Compound 89
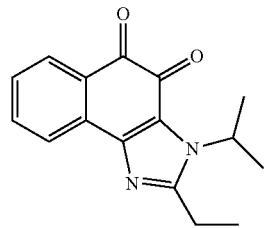
Compound 90
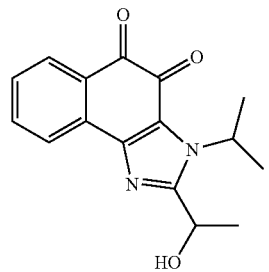
Compound 91
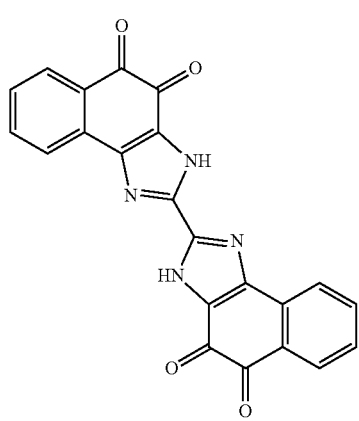
Compound 92
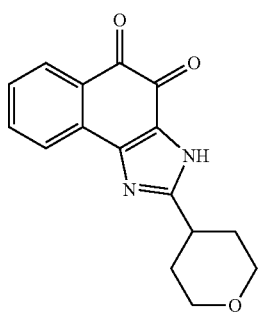
Compound 93
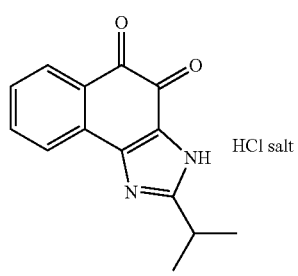
HCl salt
Compound 94
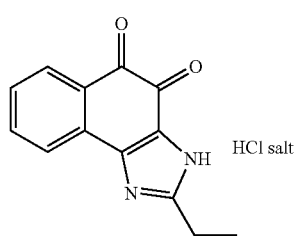
HCl salt
Compound 95
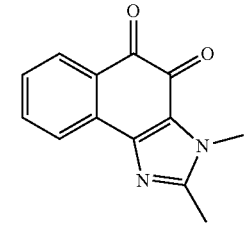
Compound 96
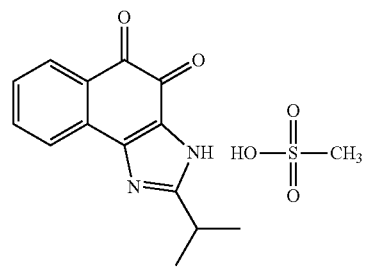
Compound 97
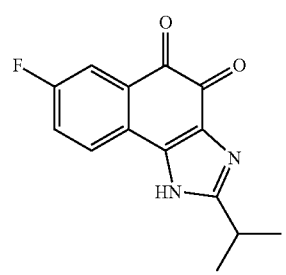

-continued
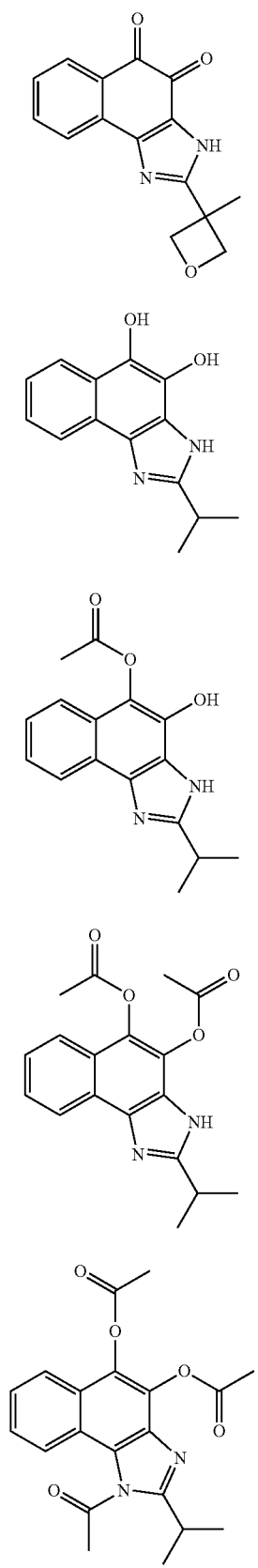
Compound 98
Compound 175
Compound 176
Compound 177
Compound 178
-continued
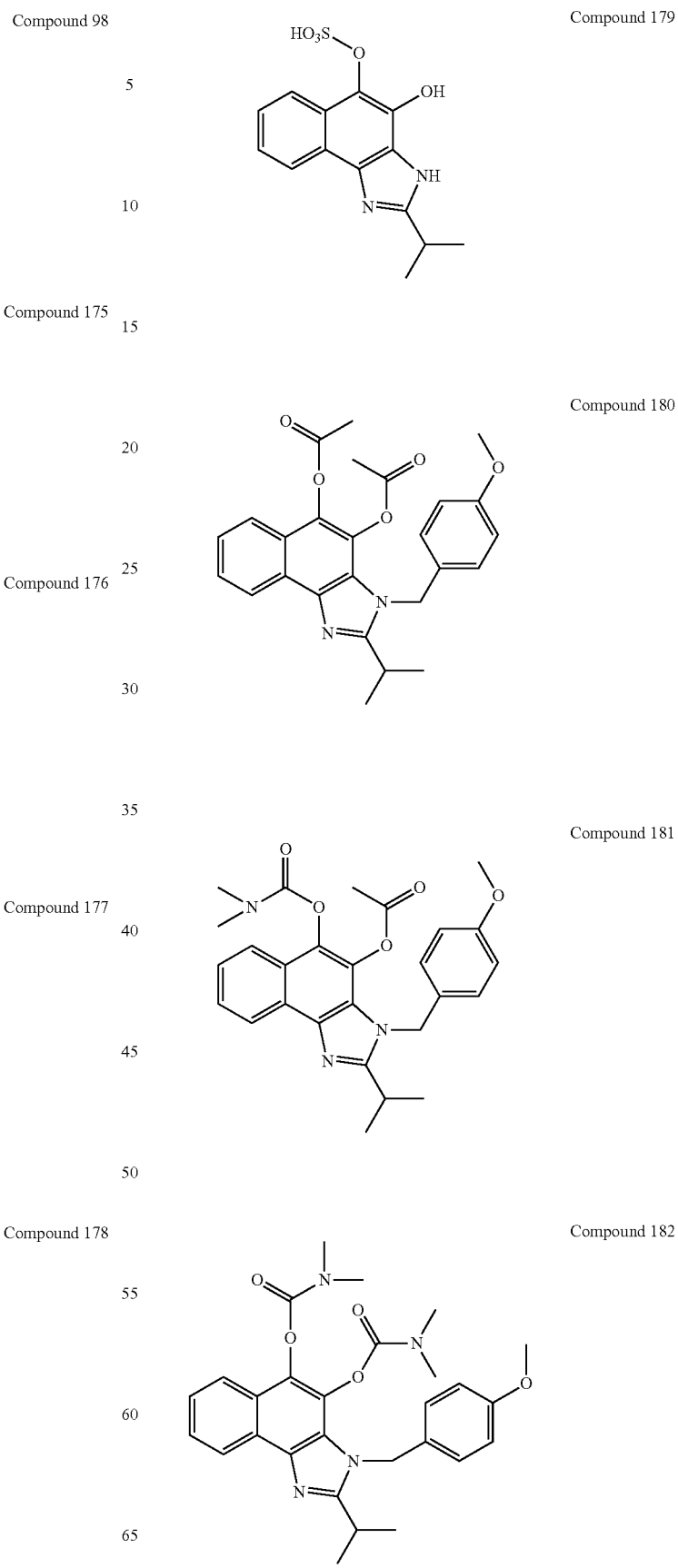
Compound 179
Compound 180
Compound 181
Compound 182

-continued

Compound 183
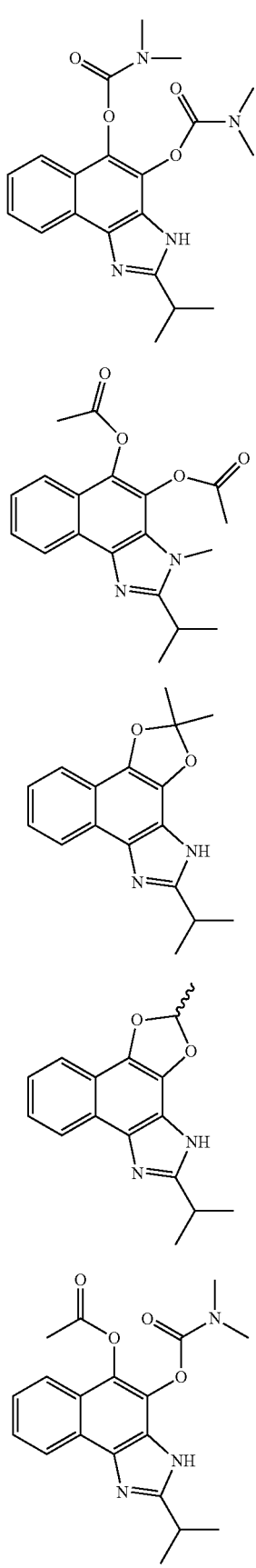
Compound 184

Compound 185

Compound 186

Compound 187

-continued

Compound 188
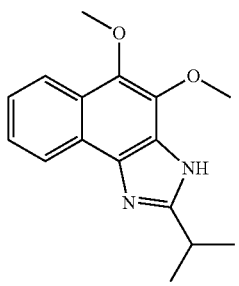

Compound 189
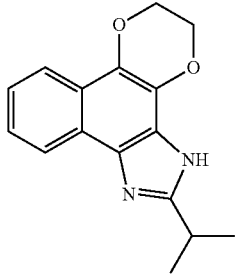

Compound 190
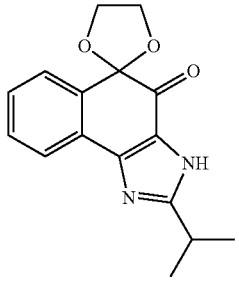

In addition, the present invention relates to a pharmaceutical for preventing or treating solid cancers or blood cancers comprising a 1,2-naphthoquinone derivative compound or a pharmaceutically acceptable salt thereof as an active ingredient, characterized in that the compound is one of the compounds represented below.

Compound 98
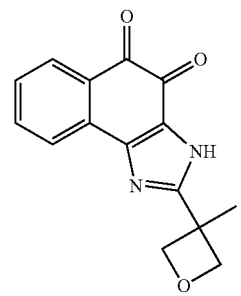

In the present invention, the solid cancer may be one or more cancers selected from the group consisting of gastric cancer, liver cancer, colon cancer, breast cancer, lung cancer, non-small cell lung cancer, pancreatic cancer, skin cancer, head and neck cancer, uterine cancer, ovarian cancer, colorectal cancer, small intestinal cancer, rectal cancer, prostate cancer, esophageal cancer, malignant lymphs, bladder cancer, gallbladder cancer, kidney cancer, and brain tumor and the like. Preferably, the cancer may be one or more cancers selected from the group consisting of lung cancer, uterine cancer, liver cancer, and breast cancer.

Among the blood cancers, the acute leukemia may be one or more cancers selected from the group consisting of acute myeloid leukemia and acute lymphocytic leukemia.

Further, the blood cancer may be drug-resistant or refractory leukemia having resistance to existing anticancer drugs. Specifically, such drug-resistant or refractory leukemia is drug-resistant refractory acute leukemia having resistance to idarubicin or cytarabine, which is a therapeutic agent for acute leukemia, or a drug-resistant chronic leukemia having resistance to imatinib, which is a therapeutic agent for chronic leukemia.

A pharmaceutically acceptable salt of the 1,2-naphthoquinone derivative compound of the present invention may include addition salts formed by inorganic acids such as hydrochloride, sulfate, phosphate, hydrobromide, hydroiodide, nitrate, pyrosulfate, or metaphosphate, addition salts formed by organic acids such as citrate, oxalate, benzoate, acetate, trifluoroacetate, propionate, succinate, fumarate, lactate, maleate, tartrate, glutarate, or sulfonate, or metal salts such as lithium salt, sodium salt, potassium salt, magnesium salt and calcium salt, but is not limited thereto.

The pharmaceutical composition according to the present invention can be formulated into a suitable form together with a commonly used pharmaceutically acceptable carrier. The "pharmaceutically acceptable" refers to being physiologically acceptable, and not usually causing an allergic reaction or a similar reaction such as gastrointestinal disorders and dizziness when administered to humans. Further, the pharmaceutical composition of the present invention may be used after being formulated into an oral preparation, such as powders, granules, tablets, capsules, suspensions, emulsions, syrups, and aerosols, etc., and a parental preparation, such as epidermal formulations, suppositories, or sterile injection solutions, in accordance with a conventional method.

Examples of carriers, excipients and diluents that can be included in the composition, may include lactose, dextrose, sucrose, sorbitol, mannitol, xylitol, erythritol, maltitol, starch, arabic gum, alginate, gelatin, calcium phosphate, calcium silicate, cellulose, methylcellulose, microcrystalline cellulose, polyvinyl pyrrolidone, water, methyl hydroxybenzoate, propyl hydroxybenzoate, talc, magnesium stearate, and mineral oil, but are not limited thereto. When formulated into a preparation, a diluting agent or an excipient, such as commonly-used fillers, stabilizing agents, binding agents, disintegrating agents, and surfactants can be used. Solid preparations for oral administration include tablets, pills, powders, granules, capsules, and the like, and these solid preparations may be prepared by mixing the compound of the present invention with at least one excipient, for example, starch, microcrystalline cellulose, sucrose, lactose, low-substituted hydroxypropyl cellulose, hypromellose or the like. In addition to the simple excipient, a lubricant such as magnesium stearate and talc are also used. Liquid preparations for oral administration include a suspension, a liquid for internal use, an emulsion, a syrup, etc. In addition to a commonly used simple diluent such as water and liquid paraffin, various excipients such as a humectant, a sweetener, an aromatic, a preservative, etc. may also be contained. Formulations for parenteral administration include a sterilized aqueous solution, a non-aqueous solution, a suspension, an emulsion, a lyophilized formulation and a suppository. The non-aqueous solution or suspension may contain propylene glycol, polyethylene glycol, a vegetable oil such as olive oil, an injectable ester such as ethyl oleate, etc. As a base of the suppository, witepsol, macrogol, tween 61, cocoa butter, laurin butter, glycerogelatin, etc. may be used. In order to formulate the formulation for parenteral administration, the 1,2-naphthoquinone derivative compound of Chemical Formula 1 or a pharmaceutically acceptable salt thereof may be mixed in water together with sterilized and/or contain adjuvants such as preservatives, stabilizers, auxiliary agents such as wettable powder or emulsifying accelerators, salt for controlling osmotic pressure and/or buffers and the like, and other therapeutically useful substances, to prepare a solution or suspension, which is then manufactured in the form of an ampoule or vial unit administration.

The pharmaceutical composition including the compound of Chemical Formula 1 disclosed herein as an active ingredient may be administered to mammals such as mice, livestock, and humans by various routes for the prevention or treatment of solid cancers or blood cancers. All modes of administration can be predicted, and for example, it can be administered by oral, rectal or intravenous, intramuscular, subcutaneous, endometrial or cerebrovascular injection. The dosage is varied depending on the age, sex, weight of the subject to be treated, the specific disease or pathological condition to be treated, the severity of the disease or pathological condition, the duration of administration, the route of administration, the drug absorption, distribution and excretion rate, the types of other drugs used, the judgment of prescriber, and the like. Dosage determination based on such factors is within the standards of those skilled in the art, and the dosage generally ranges from 0.01 mg/kg/day to approximately 2000 mg/kg/day. A more preferred dosage is 1 mg/kg/day to 500 mg/kg/day. It can be administered once a day or in several divided doses. The dosage does not limit the scope of the present invention in any way.

Advantageous Effects

The present invention relates to a pharmaceutical composition for the prevention or treatment of solid cancers or blood cancers such as acute leukemia or chronic leukemia, the pharmaceutical composition including, as an active ingredient, a 1,2-naphthoquinone derivative compound or a pharmaceutically acceptable salt thereof. When solid cancer, acute leukemia, and chronic leukemia, and drug-resistant/refractory leukemia cell lines are treated with the 1,2-naphthoquinone derivative compound, it is excellent in the effect of killing cells and thus, can be usefully used as a pharmaceutical composition for preventing or treating the carcinoma.

BRIEF DESCRIPTION OF THE DRAWINGS

FIG. 1 is a graph showing the cell viability of HL60 (FIG. 1A) or U937 (FIG. 1B) cells when treating with the compound 1 of the present invention.

FIG. 2 is a result of confirming the apoptosis or cell necrosis of KG1a cells by FACS (FIG. 2A) and a result of confirming them by Western blot (FIG. 2B), when treating with the compound 1 of the present invention.

FIG. 3 is a result of confirming the apoptosis or cell necrosis of HL60 cells by FACS (FIG. 3A) and a result of confirming them by Western blot (FIG. 3B), when treating with the compound 1 of the present invention.

FIG. 4 is a result of confirming the proliferation inhibitory effect of monocytic cells in peripheral blood (FIG. 4A) or spleen (FIGS. 4B and 4C), when treating with the compound 1 of the present invention in a mouse model of an acute leukemia in which FLT3-ITD is overexpressed.

FIG. 5 is a result of confirming the expression level of the BCR-ABL fusion gene by Western blot by treating K562 cells with the compound 1 of the present invention according to concentration.

FIG. 6 is a graph showing the cell viability of A549 (lung carcinoma) and Hela (cervix adenocarcinoma) cells by treating A549 (lung carcinoma) and Hela (cervix adenocarcinoma) with the compounds 1, 10 and 72 of the present invention.

DETAILED DESCRIPTION OF THE EMBODIMENTS

Hereinafter, preferred examples of the present invention will be described in detail. However, the present invention is not limited to the examples described herein, and can also be embodied in other forms. Rather, the content presented herein will be thorough and complete, and will fully convey the scope of the present invention to those skilled in the art.

Example 1. Synthesis of 1,2-Naphthoquinone Derivative Compound

As the 1,2-naphthoquinone derivative compound of the present invention used for confirming the therapeutic effect on acute leukemia, the compounds 1 to 98 and 175 to 190 were synthesized with reference to the method for synthesizing the compounds disclosed in Korean Patent Application Nos. 10-2014-0193184, 10-2014-0193306, 10-2014-0193370, 10-2015-0043050, and 10-2015-0043068. In addition, among the compounds prepared through the above process, the physicochemical properties for the compound 98 are shown in Table 1 below.

TABLE 1

| Compound No. | $^1$H NMR data |
| --- | --- |
| Compound 98 | $^1$H NMR (300 MHz, DMSO) δ 7.95-7.86 (m, 2H), 7.70 (t, J = 7.5 Hz, 1H), 7.45 (t, J = 7.5 Hz, 1H), 4.99 (d, J = 5.7 Hz, 2H), 4.5 (d, J = 6.0 Hz, 2H), 1.75 (s, 3H) |

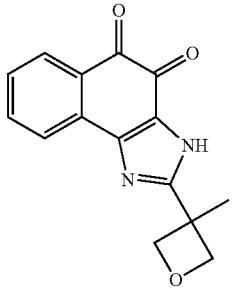

Example 2. Preparation of Acute Leukemia Cell Line, Measurement/Confirmation of Cell Viability, Apoptosis or Cell Necrosis Thereof

Example 2-1. Preparation of Acute Leukemia Cell Line

The causative factor of acute leukemia has been found to be very diverse. The constructed cell lines were also diverse. Thus, in order to confirm the applicability to a wide range of therapeutic agents that are not therapeutic agents for specific types of acute leukemia, in the present invention, KG1α cells constructed by selecting only cells having a stem cell phenotype from KG1 cells, which are cell lines obtained from a 59-year-old man with acute myelogenous leukemia, were used. HL60 cells, which are cell lines obtained from a 36-year-old woman with acute promyelocytic leukemia, and U937 cells, which are cell lines obtained from a 37-year-old man with histiocytic lymphoma, were used.

KG1α and HL60 cells were cultured in IMDM medium containing 20% FBS (fetal bovine serum), and U937 cells were cultured in RPMI 1640 medium containing 10% FBS. All cells were cultured in an incubator under conditions of 37° C. and 5% $CO_2$, and subcultured once every 2 or 3 days and used in the experiment.

Example 2-2. Measurement of Cell Viability in KG1α Cells-WST Assay

KG1α cells are cells resistant to idarubicin and cytarabine, which are the therapeutic agents for acute myeloid leukemia, and are refractory AML cells. KG1α cells cultured in Example 2-1 were cultured into a 96-well plate at $1\times10^5$ cells/well, and then cultured in an incubator at 37° C. and 5% $CO_2$ for 16 hours or more for the stabilization of cells. Subsequently, among the compounds synthesized in Example 1, the compounds 1, 10 and 72 were treated at a concentration of 0.1 to 3 μM, respectively. as shown in Table 2 below, and then cultured for 24 hours. At this time, DMSO was used as a control group. After 24 hours, each cell was treated with 10 μl of WST solution, reacted for 2 hours, and then absorbance was measured at 450 nm with a multi-scan machine, and the cell viability of KG1α cells was confirmed as shown in Table 4 below.

TABLE 2

| Condition | $IC_{50}$ (μM) |
| --- | --- |
| Compound 1 | 0.5 |

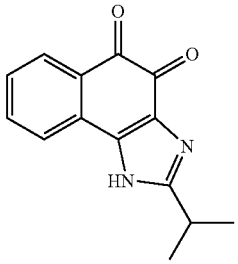

TABLE 2-continued

| Condition | IC$_{50}$ (μM) |
|---|---|
| Compound 10 | 0.5 |
| Compound 72 | 0.7 |

Table 2 shows the cell viability of KG1α cells when treated with compounds 1, 10 and 72 of the present invention as compared with the control group. The IC$_{50}$ value appeared as 0.5 to 1 μM, confirming that the effect of killing acute myeloid cells was excellent.

Example 2-3. Measurement of Cell Viability of HL60 Cells or U937 Cells

The HL60 cells or U937 cells cultured in Example 2-1 were inoculated into a 96-well plate at 1×10$^5$ cells/well, and then for the stabilization of cells, the cells were cultured in an incubator at 37° C. and 5% CO$_2$ for 16 hours or more. Subsequently, the compound 1 synthesized in Example 1 was treated at concentrations of 0.1, 0.5 and 1 μM, respectively, and reacted for 24 hours. At this time, DMSO and decitabine having a concentration of 0.1 or 1 μM was used as a control group. After 24 hours, each cell was treated with 10 μl of WST-1 solution, and reacted for 2 hours. The absorbance was then measured at 450 nm with a multi-scan machine. The cell viability of HL60 cells is shown in FIG. 1A, and the cell viability results of U937 cells are shown in FIG. 1B.

Referring to the results of FIG. 1, when HL-60 cells or U937 cells was treated with the compound 1 of the present invention, it was confirmed that it exhibited concentration-dependent cell killing effects in both HL-60 cells or U937 cells. However, when HL-60 cells or U937 cells were treated with a positive control decitabine, it exhibited concentration-dependent cell killing effects in HL60 cells, but in U937 cells, the cell killing effect was remarkably low. Therefore, it was confirmed that the 1,2-naphthoquinone derivative compound of the present invention can be usefully used as a composition for treating a wide range of acute leukemias, rather than a therapeutic agent for a specific type of acute leukemia.

Example 2-4. Confirmation of Apoptosis or Cell Necrosis in Acute Leukemia Cells Cell death was typically known as apoptosis or cell necrosis. Thus, in order to confirm whether the death of acute leukemia cells induced by the compound 1 of the present invention was due to apoptosis or cell necrosis, fluorescence activated cell sorting (FACS) and western blot were performed.

First, in order to conduct FACS, KG1α cells or HL60 cells cultured in Example 1-2 were inoculated in a 6-well plate at 1×10$^7$ cells/well, and for the stabilization of cells, the cells were cultured in an incubator at 37° C. and 5% CO$_2$ for 16 hours or more. Subsequently, the compound 1 was treated at concentrations of 0, 0.1, 0.5, 1 and 2 μM, respectively, and cultured for 24 hours, and then the cells were recovered and washed with cold PBS. Only 1×10$^6$ cells were taken and resuspended with PBS, and then stained with Annexin-V (green fluorescence), which increases during apoptosis, and Pi (propidium iodide, red fluorescence), which reacts during apoptosis. The degree of the two indicators were quantified by FACS, the FACS results for KG1α cells are shown in FIG. 2A, and the FACS results for HL60 cells are shown in FIG. 3A.

Next, in order to perform western blot, KG1α cells or HL60 cells cultured in Example 2-1 were inoculated into a 6-well plate at 1×10$^7$ cells/well. In order to stabilize the cells, the cells were cultured for 16 hours or more in an incubator at 37° C. and 5% CO$_2$. Then, the compound 1 was treated at concentrations of 0, 0.1, 0.5, 1 and 2 μM, respectively, and cultured for 24 hours, and then only cells were recovered. The protein extraction buffer was added to the cells obtained in the above process, and then reacted on ice for 30 minutes to break the cell membrane and centrifuged to take only the supernatant, and then extract the protein. SDS-PAGE was performed using the extracted protein, and then transferred to the nitrocellular membrane. Then, after reacting a specific antibody related to apoptosis, the amount of the protein was confirmed using the ECL buffer, and the results of Western blotting of KG1α cells are shown in FIG. 2B, and the results of Western blotting of HL60 cells are shown in FIG. 3B.

Referring to the results of FIGS. 2 and 3, when U937 cells or A549 cells were treated with the compound 1 of the present invention, in KG1α cells, acute leukemia cells died due to apoptosis, but in HL60 cells, both apoptosis and cell necrosis occurred, confirming that acute leukemia cells died.

Example 3. Confirmation of Changes in Monocyte Cells in Acute Leukemia Model In order to confirm the change in the expression of the FLT3-ITD gene by Compound 1 of the present invention, peripheral blood and spleen were collected after 8 weeks from the animals of an experimental group in which Compound 1 of the present invention was mixed and administered in a diet at a concentration of 120 mg/kg using a mouse (jackson lab) that systemically overexpressed FLT3-ITD, and a control group to which only a solvent was administered (untreated group).

In the case of peripheral blood, cold 1×PBS was added to a small amount of blood, centrifuged, washed, to which RBC lysis buffer was added and reacted for 5 minutes at room temperature to remove red blood cells. After adding cold 1×PBS again, the pellet from which the supernatant had been removed by centrifugation was resuspended in 1×PBS containing 1% FBS. Only 1×10$^6$ cells were taken, and Gr-1 and Mac-1 antibodies, which were specifically expressed in granulocytes, and CD3 antibody specifically expressed in monocytes, were simultaneously immuno-stained. The antibodies were reacted on ice at a ratio of 1:200 for 20 minutes, washed with 1×PBS, then resuspended with 1×PBS containing 1% FBS, and quantified by FACS, and shown in FIG. 4A.

In the case of the spleen, the cells were crushed on a mesh having a 40 µm hole, separated into single cells, and then washed with cold 1×PBS to which RBC lysis buffer was added and reacted at room temperature for 5 minutes to remove red blood cells. After washing again with cold 1×PBS, the pellet was resuspended in 1×PBS containing 1% FBS. Only 1×10$^6$ cells were taken, and Gr-1 and Mac-1 antibodies, which were specifically expressed in granulocytes, and CD3 antibody specifically expressed in monocytes, were simultaneously immuno-stained. The antibodies were reacted on ice at a ratio of 1:200 for 20 minutes, washed with 1×PBS, resuspended in 1×PBS containing 1% FBS, and quantified by FACS, and shown in FIGS. 4B and 4C.

Referring to the results of FIG. 4, when the compound 1 of the present invention was treated in an acute myelogenous leukemia mouse model in which FLT3-ITD was overexpressed, it was confirmed that it had an excellent effect of suppressing the proliferation of monocyte cells (acute leukemia) in both peripheral blood and spleen, and thus had an effect of improving acute myeloid leukemia.

Example 4. Preparation of Chronic Leukemia Cell Line and Measurement of Cell Viability Thereof

Example 4-1. Preparation of Chronic Leukemia Cell Lines

K562 cells obtained from a 53-year-old woman with chronic myeloid leukemia were cultured in an incubator under conditions of 37° C. and 5% CO$_2$ using RPMI medium containing 10% FBS (fetal bovine serum), and subcultured once every two days and used in the experiment.

Example 4-2. Measurement of Cell Viability in Chronic Leukemia Cells-WST Assay The K562 cells cultured in Example 4-1 were inoculated into a 96-well plate at 1×10$^5$ cells/well, and then, for the stabilization of cells, the cells were cultured in an incubator at 37° C. and 5% CO$_2$ for 16 hours or more. Subsequently, among the compounds synthesized in Example 1, the compounds 1, 10, and 72 and 192 were treated at a concentration of 0.1 to 5 µM and then cultured for 4 hours. At this time, DMSO was used as a control group. After 4 hours of incubation, 10 µl of WST solution was added to each cell and then reacted for 2 hours. The absorbance was then measured at 450 nm with a multi-scan machine, and the cell viability of K562 cells is shown in Table 3 below.

TABLE 3

| Condition | IC$_{50}$ (µM) |
| --- | --- |
| Compound 1 | 1.6 |
| Compound 10 | 0.9 |
| Compound 72 | 1.4 |

Referring to Table 3 above, when K562 cells were treated with the compounds 1, 10, and 72 of the present invention, it was confirmed that the IC$_{50}$ value appeared as 1 to 2 µM, confirming that the effect of killing chronic myelogenous leukemia cells was excellent, as compared with the control group.

Example 5. Confirmation of Expression Level of BCR-ABL Fusion Gene in Chronic Myelogenous Leukemia Cells The BCR-ABL fusion gene, existing only in chronic myelogenous leukemia, generated and transmitted continuous cell growth signals to induce the growth of cancer cells. Thus, after chronic myeloid leukemia cells were treated with the compound of the present invention, western blot was used to confirm whether the expression level of the BCR-ABL fusion gene was reduced.

First, the K562 cells cultured in Example 4-1 were inoculated into a 60 mm plate at 5×10$^6$ cells/well, and then for the stabilization of cells, the cells were cultured in an incubator at 37° C. and 5% CO$_2$ for 16 hours or more. The, the compound 1 was treated at concentrations of 0.5, 1, 1.5, 2 and 2.5 µM, respectively, and cultured for 6 hours, and then the cells were recovered. A protein extraction buffer (RIPA buffer) was added to the cells obtained in the above process, and reacted on ice for 30 minutes to break the cell membrane, which was centrifuged to remove a supernatant, and then the protein was extracted. The extracted protein was developed by electrophoresis using SDS-PAGE, and then transferred to the PVDF membrane. Then, the antibody related to the BCR-ABL fusion gene was reacted, and then the amount of the protein was confirmed using the ECL buffer, and Western blot results for the K562 cell line are shown in FIG. 5.

Referring to the results of FIG. 5, when K562 cells were treated with the compound 1 of the present invention, it was confirmed that the expression level of the BCR-ABL fusion gene, which plays the most important role in the onset of chronic myelogenous leukemia, was decreased in a concentration-dependent manner. In addition, it can be seen that due to the decrease in the expression of the BCR-ABL fusion gene, the expression of phospho-bcr-abl and phospho-stat5, which indicates the activity of the BCR-ABL fusion gene (a signal that induces cell growth), was also decreased.

However, the expression level of the BCR-ABL fusion gene, which is a cancer-causing gene, decreased, whereas in the case of c-abl protein present in normal blood cells, the expression level was not affected. Thus, it was confirmed that the compound of the present invention does not affect the c-abl protein expressed in normal cells, and the composition selectively reduces only the BCR-ABL fusion protein which is a cancer-causing gene existing only in chronic myelogenous leukemia.

Example 6. Preparation of Solid Cancer Cell Lines and Measurement of Cell Viability Thereof

Example 6-1. Preparation of Solid Cancer Cell Lines

To confirm the possibility of use as a therapeutic agent for solid cancer, A549 cell line obtained from a 58-year-old men with lung carcinoma, Hela cell line obtained from a 31-year-old women with cervix adenocarcinoma, HepG2 cell line obtained from a 15-year-old boy with hepatocellular carcinoma, MCF7 cell line obtained from a 69-year-old woman with breast adenocarcinoma, and Beas-2B cell line obtained from a normal lung for comparison with solid cancer cell line were used.

The A549 (lung carcinoma), Hela (cervix adenocarcinoma), HepG2 (hepatocellular carcinoma), MCF7 (breast carcinoma), and Beas-2B (normal lung) cell lines were used in DMEM medium containing 10% FBS, subcultured once every 2 days in an incubator under conditions of 37° C. and 5% $CO_2$ and used in the experiment.

Example 6-2. Measurement of Cell Viability in Solid Cancer Cells-WST Assay

A549 (lung carcinoma), Hela (cervix adenocarcinoma), HepG2 (hepatocellular carcinoma), MCF7 (breast carcinoma), and Beas-2B (normal lung) cells cultured in Example 6-1 were inoculated into a 96-well plated at $1 \times 10^4$ cells/well, and then for the stabilization of cells, the cells were cultured in an incubator at 37° C. and 5% $CO_2$ for 16 hours or more. Subsequently, among the compounds synthesized in Example 1, the compounds 1, 10 and 72 were treated at a concentration of 1 to 30 µM, and then cultured for 6 hours. At this time, DMSO and β-lapachone were used as the control group. After 4 hours of incubation, 10 µl of WST solution was added to each cell, the reaction was carried out for 2 hours, and the absorbance was measured at 450 nm with a multi-scan machine. The cell viabilities of A549 (lung carcinoma), Hela (cervix adenocarcinoma), HepG2 (hepatocellular carcinoma) and MCF7 (breast carcinoma) cells are shown in Table 4 and FIG. 6 below.

TABLE 4

| Condition | IC$_{50}$ (µM) | | | |
| --- | --- | --- | --- | --- |
| | A549 | Hela | HepG2 | MCF7 |
| Positive control group (beta-rapacon) | 5.0 | 4.8 | 12.3 | 13.2 |
| Compound 1 | 5.1 | 4.6 | 10.1 | 14.4 |
| Compound 10 | 5.5 | 7.7 | 12.1 | 14.1 |
| Compound 72 | 6.5 | 9.1 | 12.6 | 12.5 |

Referring to Table 4 and FIG. 6, when A549 (lung carcinoma), Hela (cervix adenocarcinoma), HepG2 (hepatocellular carcinoma), MCF7 (breast carcinoma) and Beas-2B (normal lung) cells were treated with the compounds 1, 10 and 72 of the present invention for 6 hours, it was confirmed that they exhibited a killing effect similar to β-lapachone, and thus, the compounds of the present invention had a therapeutic effect on solid cancer, as compared with the control group.

Further, although not shown in Table 4, when Beas-2B which is a normal lung cell line was treated with the compounds of the present invention, the average cell viability was 80% or more, but when treating A549 which is a lung carcinoma, it exhibited the cell viability of about 50%. Thus, since the 1,2-naphthoquinone derivative compound of the present invention did not exhibit cytotoxicity to normal cells but specifically exhibited apoptosis effect on cancer cells, it can be confirmed that it can be usefully used as a composition for the treatment of various solid cancers.

Example 7. Toxicity Experiment

This experiment was conducted to examine the acute toxicity to the animal body acutely (within 24 hours) when the compound 1 of the present invention was ingested in excess in a short period of time, and to determine the mortality rate. 20 $C_{57}BL/6$ mice, which are common mice, were prepared, and ten mice were assigned to each group. Only 0.1% SLS (sodium lauryl sulfate) was administered to the control group, and the compound 1 was orally administered to the experimental group at a concentration of 120 mg/kg, respectively. As a result of examining each mortality rate 24 hours after administration, both the control group and the experimental group to which the compound 1 was administered survived.

Formulation Example 1. Preparation of Pharmaceutical Formulation Containing the Compound of the Present Invention Formulation Example 1-1. Preparation of Powder 2 g of the compound 1 of the present invention and 1 g of lactose were mixed and filled in an airtight cloth to prepare a powder.

Formulation Example 1-2. Preparation of Tablets 100 mg of the compound 1 of the present invention, 100 mg of microcrystalline cellulose, 60 mg of lactose hydrate, 20 mg of low-substituted hydroxypropyl cellulose, and 2 mg of magnesium stearate were mixed, and then the mixture was tableted according to a conventional tablet preparation method to prepare tablets.

Formulation Example 1-3. Preparation of Capsules 100 mg of the compound 1 of the present invention, 100 mg of microcrystalline cellulose, 60 mg of lactose hydrate, 20 mg of low-substituted hydroxypropyl cellulose, and 2 mg of magnesium stearate were mixed, and then the above ingredients were mixed according to a conventional capsule preparation method and filled into gelatin capsules to prepare capsules.

Formulation Example 1-4. Preparation of Injections 10 mg of the compound 1 of the present invention, an appropriate amount of injectable sterilized distilled water and an appropriate amount of a pH adjuster were mixed, and then injections were prepared in the amount of the above components per ampoule (2 ml) according to a conventional method for preparing injections.

The invention claimed is:
1. A method for treating solid cancers or blood cancers, comprising, administering to a subject a therapeutically effective amount of a pharmaceutical composition comprising, as an active ingredient, a 1,2-naphthoquinone derivative compound represented by the following Chemical Formula 1 or a pharmaceutically acceptable salt thereof:

[Chemical Formula 1]

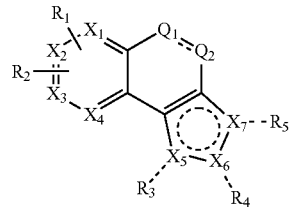

wherein:
$R_1$ and $R_2$ are each independently hydrogen, halogen, hydroxy, $C_1$-$C_6$ alkoxy, $C_1$-$C_6$ alkyl, $C_4$-$C_{10}$ aryl, $C_4$-$C_{10}$ aryloxy, $C_2$-$C_{10}$ heteroaryl, —$NO_2$, —$NR'_1R'_2$, —$NR'_1(CO(O)R'_2)$, —$NR'_1(C(O)NR'_1R'_2)$, —$CO(O)R'_1$, —$C(O)NR'_1R'_2$, —CN, —$SO(O)R'_1$, —$SO(O)NR'_1R'_2$, —$NR'_1(SO(O)R'_2)$, —$CSNR'_1R'_2$, or $R_1$ and $R_2$ taken together form a cyclic structure of $C_4$-$C_{10}$ aryl or a cyclic structure of $C_2$-$C_{10}$ heteroaryl, wherein $R'_1$ and $R'_2$ are each independently hydrogen, $C_1$-$C_6$ alkyl, $C_3$-$C_8$ cycloalkyl, or $C_4$-$C_{10}$ aryl, $C_4$-$C_{10}$ aryloxy, $C_1$-$C_8$ heteroaryl, —$(CR''_1R''_2)_m$—$C_4$-$C_{10}$ aryl, —$(CR''_1R''_2)_m$—$C_4$-$C_{10}$ heteroaryl or $NR''_1R''_2$, the $R''_1$ and $R''_2$ are each independently hydrogen, $C_1$-$C_3$ alkyl, or $R''_1$ and $R''_2$ taken together form a cyclic structure of $C_4$-$C_{10}$ aryl;
$R_3$, $R_4$ and $R_5$ are each independently hydrogen, halogen, hydroxy, $C_1$-$C_6$ alkyl, $C_2$-$C_{10}$ alkene, $C_1$-$C_6$ alkoxy, $C_3$-$C_8$ cycloalkyl, $C_2$-$C_8$ heterocycloalkyl, $C_4$-$C_{10}$ aryl, $C_4$-$C_{10}$ aryloxy, $C_1$-$C_8$ heteroaryl, —$(CR'_5R'_6)_m$—$C_4$-$C_{10}$ aryl, —$(CR'_5R'_6)_m$—$C_4$-$C_{10}$ aryloxy, —$(CR'_5R'_6)_m$—$C_1$-$C_8$ heteroaryl, —$(CR'_5R'_6)_m$—$NR'_3R'_4$, —$(CR'_5R'_6)_m$—$C_3$-$C_8$ heterocycloalkyl, —$(CR'_5R'_6)_m$—$OR'_3$, —$(CR'_5R'_6)_m(O)COR'_3$, —$CO(O)R'_3$, —$CONR'_3R'_4$, —$NR'_3R'_4$, —$NR'_3(C(O)R'_4)$, —$SO(O)R'_3$, —$SO(O)NR'_3R'_4$, —$NR'_3(SO(O)R'_4)$, —$CSNR'_3R'_4$, —$CH_2A$ where the compound of Chemical Formula 1 is "A", or -A where the compound of Chemical Formula 1 is "A", wherein the $R'_3$ and $R'_4$ are each independently hydrogen, $C_1$-$C_6$ alkyl, $C_3$-$C_8$ cycloalkyl, $C_4$-$C_{10}$ aryl, —$(CR'_5R'_6)_m$—$C_4$-$C_{10}$ aryl, —$(CR'_5R'_6)_m$—$C_4$-$C_{10}$ aryloxy, —$(CR'_5R'_6)_m$—$C_1$-$C_{10}$ heteroaryl, —$CO(O)R''_3$, or, $R'_3$ and $R'_4$ taken together form a cyclic structure of $C_2$-$C_{10}$ heterocycloalkyl, or a cyclic structure of $C_1$-$C_{10}$ heteroaryl, the $R'_5$ and $R'_6$ are each independently hydrogen or $C_1$-$C_3$ alkyl, the $R''_3$ is $C_1$-$C_6$ akyl;
$Q_1$ and $Q_2$ are each independently CO, $COR_6$, or $COR_7$, when $Q_1$ is CO and $Q_2$ is CO, $Q_1$ and $Q_2$ form a single bond, when $Q_1$ is $COR_6$ and $Q_2$ is $COR_7$, $Q_1$ and $Q_2$ form a double bond;
$R_6$ and $R_7$ are each independently hydrogen, $C_1$-$C_{10}$ alkoxy, $C_1$-$C_6$ alkyl, $C_4$-$C_{10}$ aryl, $C_4$-$C_{10}$ aryloxy, $C_2$-$C_{10}$ heteroaryl, —$CO(O)R'_7$, —$C(O)NR'_7R'_8$, —$SO(O)R'_7$, —$SO(O)NR'_7R'_8$, —$SO_3R'_7$, —$PO_3R'_7$, —$CSNR'_7R'_8$, or $R_6$ and $R_7$ taken together form a cyclic structure of $C_3$-$C_{10}$ heterocycloalkyl, or a cyclic structure of $C_3$-$C_{10}$ heteroaryl, the $R'_7$ and $R'_8$ are each independently hydrogen, $C_1$-$C_6$ alkyl, $C_3$-$C_8$ cycloalkyl, $C_4$-$C_{10}$ aryl, $C_4$-$C_{10}$ aryloxy, $C_1$-$C_8$ heteroaryl, —$(CR''_4R''_5)_m'$—$C_4$-$C_{10}$ aryl, the $R''_4$ and $R''_5$ are each independently hydrogen, $C_1$-$C_3$ alkoxy;
m and m' are each independently an integer of 1 to 4;
the hetero atom is at least one selected from N, O and S;
$X_1$ to $X_4$ are each independently CH or $N(R''_6)$;

$X_5$ is N, $X_6$ is C, $X_7$ is N, wherein $R''_6$ is hydrogen or $C_1$-$C_3$ alkyl;

in the Chemical Formula, the notation ==== means a single bond or a double bond, the notation ---- means that a single bond or a bond may not be formed, the notation ⌒ means that the cyclic structure may be or may not be aromatic; and the substituted means being substituted with one or more substituents selected from the group consisting of hydroxy, halogen element, $C_1$-$C_{10}$ alkyl, $C_2$-$C_{10}$ alkenyl, $C_2$-$C_{10}$ alkynyl, $C_1$-$C_{10}$ alkoxy, $C_1$-$C_{10}$ alkoxycarbonyl, $C_3$-$C_8$ cycloalkyl, $C_2$-$C_8$ heterocycloalkyl, $C_4$-$C_{10}$ aryl, and $C_2$-$C_{10}$ heteroaryl;

wherein the blood cancer is selected from the group consisting of acute leukemia, chronic leukemia and drug-resistant chronic leukemia or refractory acute leukemia;

the chronic leukemia is selected from the group consisting of chronic myelogenous leukemia or chronic lymphocytic leukemia;

the acute leukemia is selected from the group consisting of acute myelogenous leukemia or acute lymphocytic leukemia; and the solid cancer is selected from the group consisting of lung cancer, uterine cancer, liver cancer and breast cancer.

2. The method according to claim 1, wherein the pharmaceutical composition comprises, as an active ingredient, a 1,2-naphthoquinone derivative compound represented by the Chemical Formula 1 or a pharmaceutically acceptable salt thereof, wherein:

$R_3$ is hydrogen, halogen, hydroxy, $C_1$-$C_6$ alkyl, $C_1$-$C_6$ alkoxy, $C_3$-$C_8$ cycloalkyl, $(CR'_5R'_6)_m$—$C_4$-$C_{10}$ aryl, —$(CR'_5R'_6)_m$—$OR'_3$, —$CO(O)R'_3$, —$CH_2A$ where the compound of Chemical Formula 1 is "A", or -A where the compound of Chemical Formula 1 is "A", wherein $R'_3$ is hydrogen, $C_1$-$C_6$ alkyl, $C_3$-$C_8$ cycloalkyl, $C_4$-$C_{10}$ aryl, —$(CR'_5R'_6)_m$—$C_4$-$C_{10}$ aryl, —$(CR'_5R'_6)_m$—$C_4$-$C_{10}$ aryloxy, —$(CR'_5R'_6)_m$—$C_1$-$C_{10}$ heteroaryl, —CO(O)$R''_3$, the $R'_5$ and $R'_6$ are each independently hydrogen, $C_1$-$C_6$ alkyl, the $R''_3$ is $C_1$-$C_6$ akyl;

$R_4$ is hydrogen, halogen, hydroxy, $C_1$-$C_6$ alkyl, $C_2$-$C_{10}$ alkene, $C_1$-$C_6$ alkoxy, $C_3$-$C_8$ cycloalkyl, $C_2$-$C_8$ heterocycloalkyl, $C_4$-$C_{10}$ aryl, $C_4$-$C_{10}$ aryloxy, $C_1$-$C_8$ heteroaryl, —$(CR'_5R'_6)_m$—$C_4$-$C_{10}$ aryl, —$(CR'_5R'_6)_m$—$C_4$-$C_{10}$ aryloxy, —$(CR'_5R'_6)_m$—$C_1$-$C_8$ heteroaryl, —$(CR'_5R'_6)_m$—$NR'_3R'_4$, —$(CR'_5R'_6)_m$—$C_3$-$C_8$ heterocycloalkyl, —$(CR'_5R'_6)_m$—$OR'_3$, —$(CR'_5R'_6)_m(O)COR'_3$, —$CO(O)R'_3$, —$CONR'_3R'_4$, —$NR'_3R'_4$, —$NR'_3(C(O)R'_4)$, -A where the compound of Chemical Formula 1 is "A", wherein $R'_3$ and $R'_4$ are each independently hydrogen, $C_1$-$C_6$ alkyl, $C_3$-$C_8$ cycloalkyl, $C_4$-$C_{10}$ aryl, —$(CR'_5R'_6)_m$—$C_4$-$C_{10}$ aryl, —$(CR'_5R'_6)_m$—$C_4$-$C_{10}$ aryloxy, —$(CR'_5R'_6)_m$—$C_1$-$C_{10}$ heteroaryl, —CO(O)$R''_3$, or $R'_3$ and $R'_4$ taken together form a cyclic structure of $C_2$-$C_{10}$ heterocycloalkyl, or a cyclic structure of $C_1$-$C_{10}$ heteroaryl, the $R'_5$ and $R'_6$ are each independently hydrogen or $C_1$-$C_3$ alkyl, the $R''_3$ is $C_1$-$C_6$ akyl;

$R_5$ is hydrogen, halogen, hydroxy, $C_1$-$C_6$ alkyl, $C_2$-$C_{10}$ alkene, $C_1$-$C_6$ alkoxy, $C_3$-$C_8$ cycloalkyl, $C_2$-$C_8$ heterocycloalkyl, $C_4$-$C_{10}$ aryl, $C_4$-$C_{10}$ aryloxy, $C_1$-$C_8$ heteroaryl, —$(CR'_5R'_6)_m$—$C_4$-$C_{10}$ aryl, —$(CR'_5R'_6)_m$—$C_4$-$C_{10}$ aryloxy, —$(CR'_5R'_6)_m$—$C_1$-$C_8$ heteroaryl, —$(CR'_5R'_6)_m$—$NR'_3R'_4$, —$(CR'_5R'_6)_m$—$C_3$-$C_8$ heterocycloalkyl, —$(CR'_5R'_6)_m$—$OR'_3$, —$(CR'_5R'_6)_m(O)COR'_3$, —$CO(O)R'_3$, —$CONR'_3R'_4$, —$NR'_3R'_4$, —$NR'_3(C(O)R'_4)$, —$CH_2A$ where the compound of Chemical Formula 1 is "A", wherein $R'_3$ and $R'_4$ are each independently hydrogen, $C_1$-$C_6$ alkyl, $C_3$-$C_8$ cycloalkyl, $C_4$-$C_{10}$ aryl, —$(CR'_5R'_6)_m$—$C_4$-$C_{10}$ aryl, —$(CR'_5R'_6)_m$—$C_4$-$C_{10}$ aryloxy, —$(CR'_5R'_6)_m$—$C_1$-$C_{10}$ heteroaryl, —CO(O)$R''_3$, or $R'_3$ and $R'_4$ taken together form a cyclic structure of $C_2$-$C_{10}$ heterocycloalkyl, or a cyclic structure of $C_1$-$C_{10}$ heteroaryl, the $R'_5$ and $R'_6$ are each independently hydrogen or $C_1$-$C_3$ alkyl, and the $R''_3$ is $C_1$-$C_6$ akyl.

3. The method according to claim 1, wherein the pharmaceutical composition comprises, as an active ingredient, a 1,2-naphthoquinone derivative compound represented by the Chemical Formula 1 or a pharmaceutically acceptable salt thereof, wherein the compound of the Chemical Formula 1 is one of the compounds represented below:

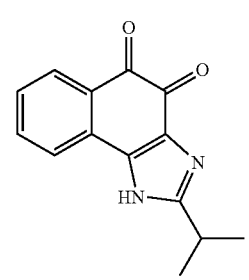

Compound 1

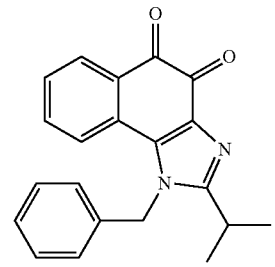

Compound 2

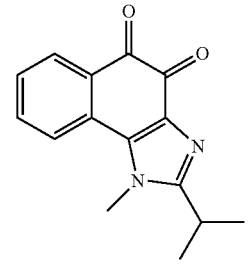

Compound 3

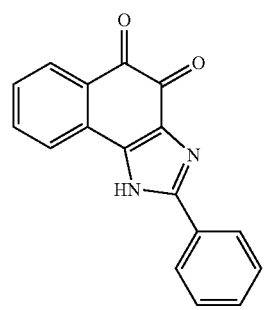

Compound 4

-continued
Compound 5
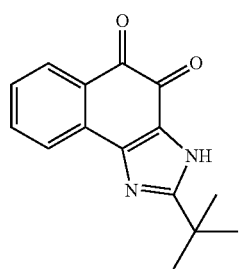
Compound 6
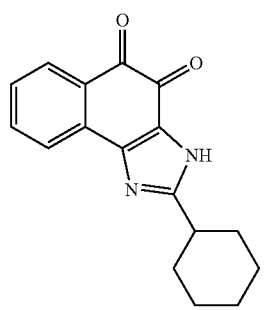
Compound 7
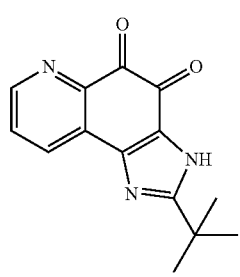
Compound 8
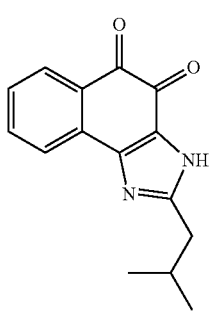
Compound 9
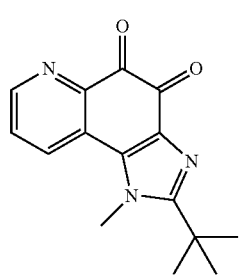
-continued
Compound 10
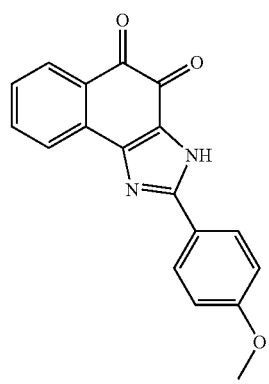
Compound 11
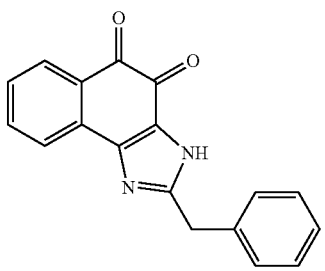
Compound 12
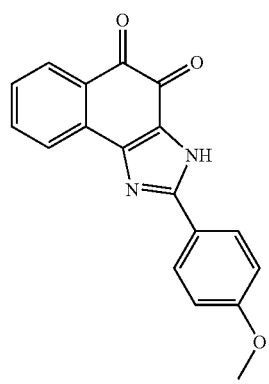
Compound 13
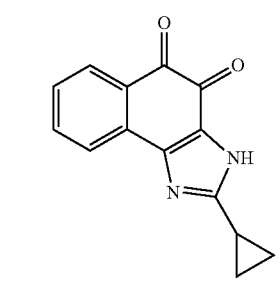
Compound 14
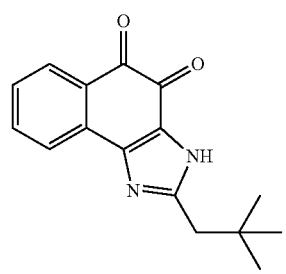

Compound 15
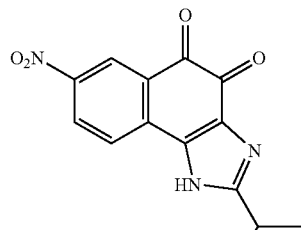
Compound 16
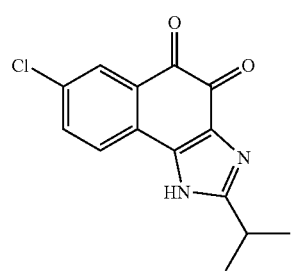
Compound 17
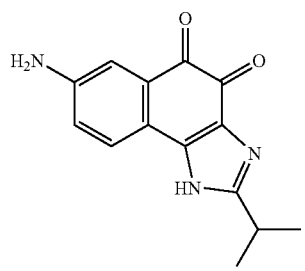
Compound 18
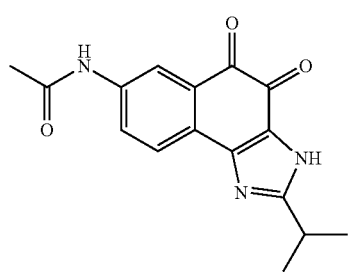
Compound 19
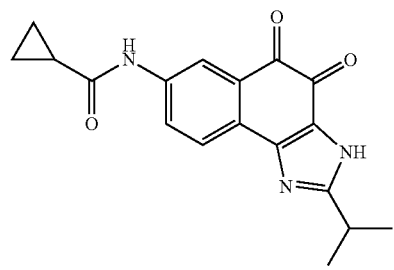
Compound 20
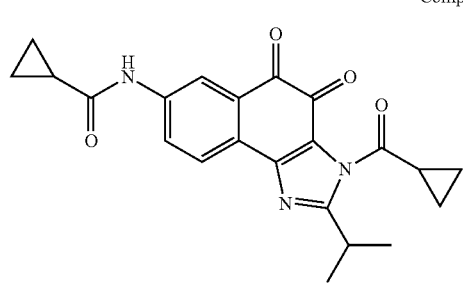
Compound 21
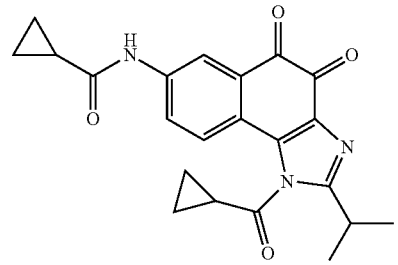
Compound 22
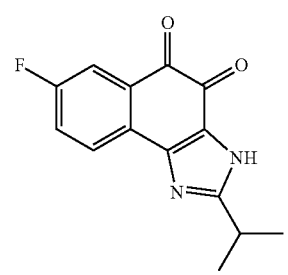
Compound 23
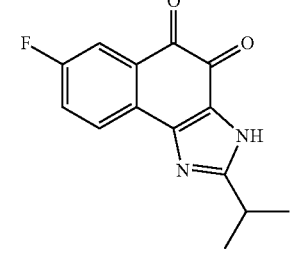
Compound 24
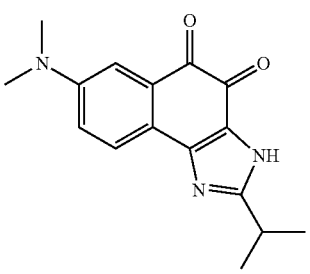
Compound 25
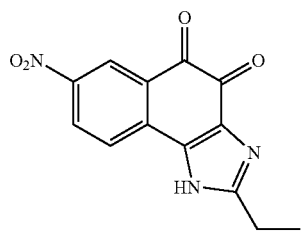
Compound 26
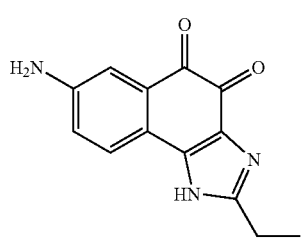

Compound 27
Compound 28
Compound 29
Compound 30
Compound 31
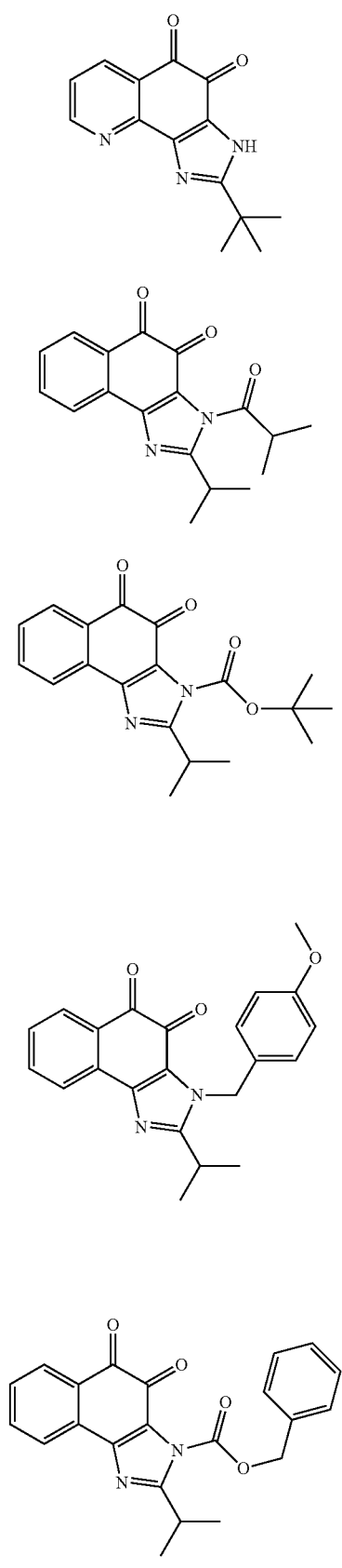
Compound 32
Compound 33
Compound 34
Compound 35
Compound 36
Compound 37
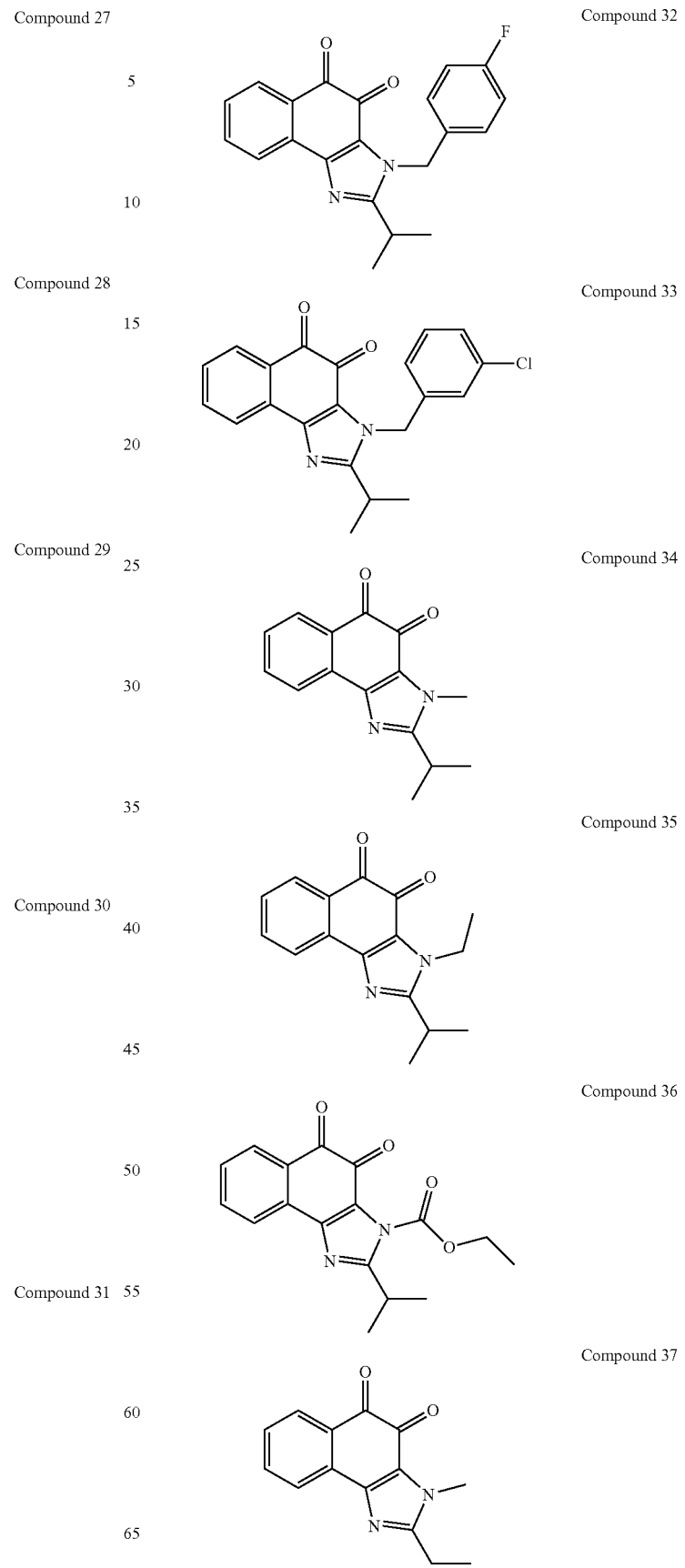

-continued
Compound 38
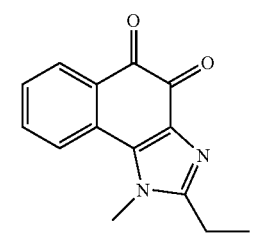
Compound 39
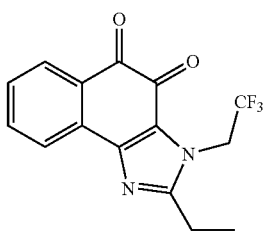
Compound 40
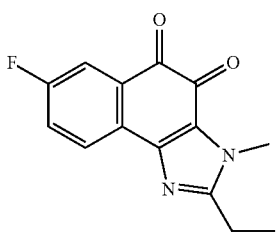
Compound 41
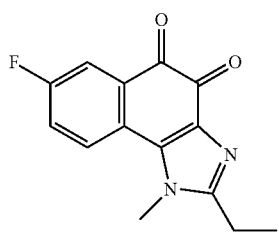
Compound 42
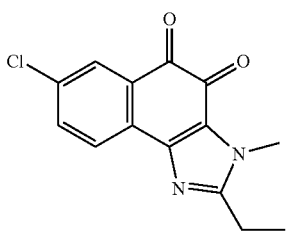
Compound 43
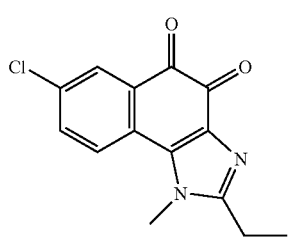
-continued
Compound 44
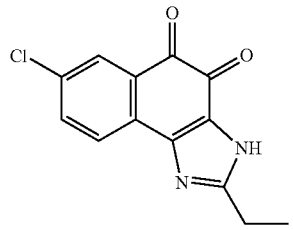
Compound 45
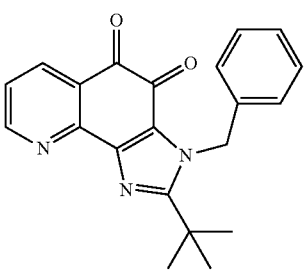
Compound 46
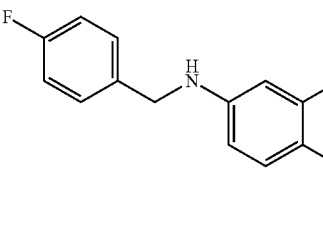
Compound 47
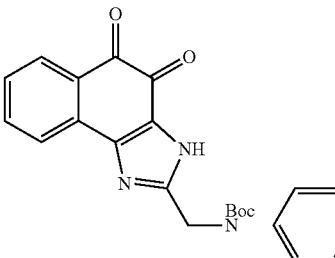
Compound 48
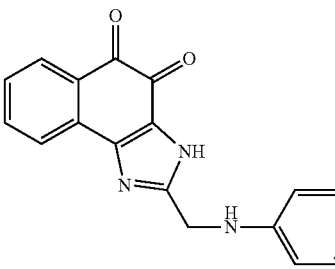
Compound 49
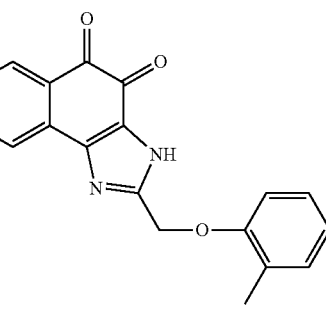

Compound 50
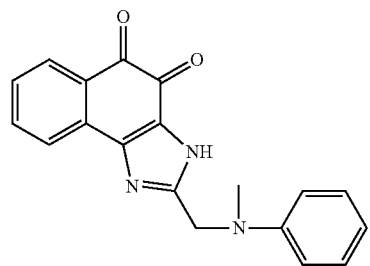
Compound 51
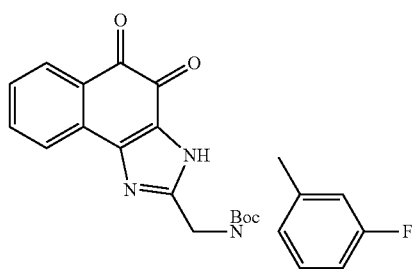
Compound 52
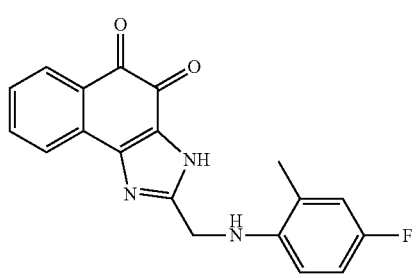
Compound 53
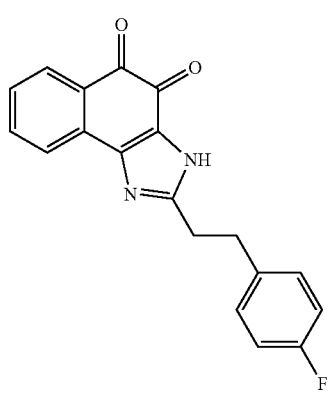
Compound 54
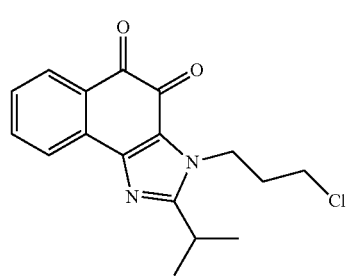
Compound 55
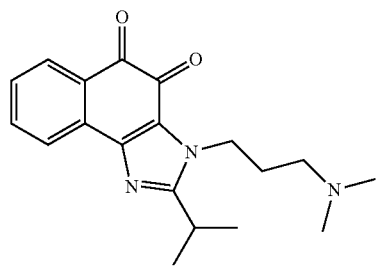
Compound 56
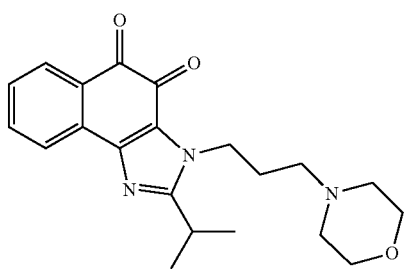
Compound 57
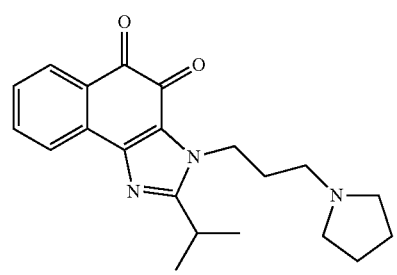
Compound 58
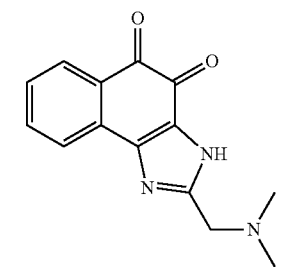
Compound 59
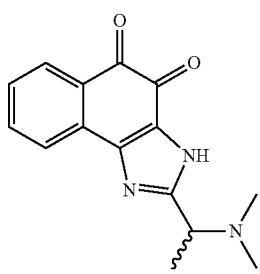
Compound 60
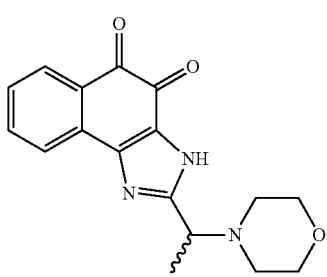

Compound 61
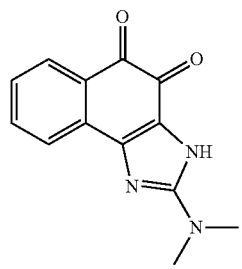
Compound 62
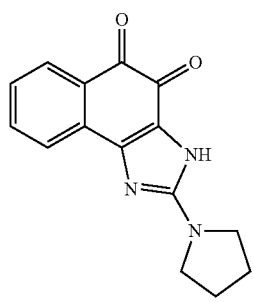
Compound 63
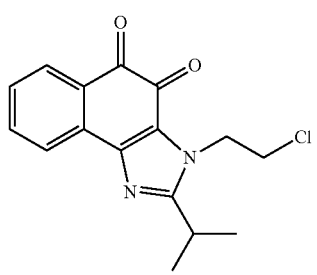
Compound 64
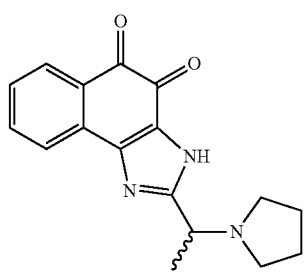
Compound 65
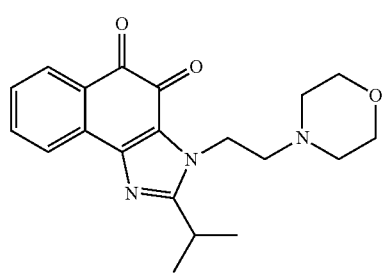
Compound 66
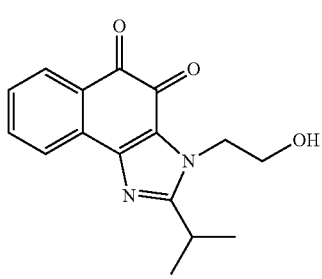
Compound 67
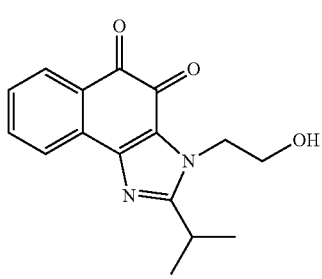
Compound 68
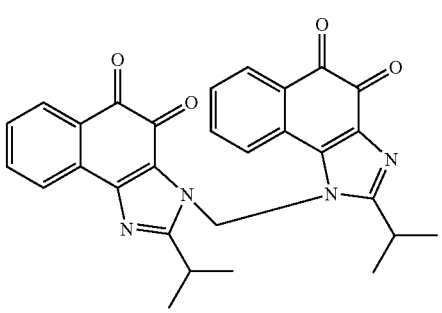
Compound 69
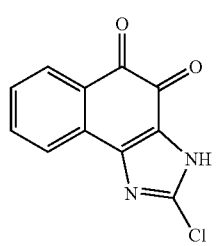
Compound 70
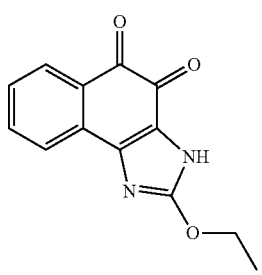

Compound 71
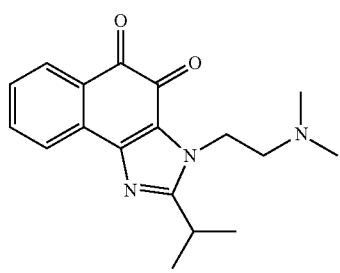
Compound 72
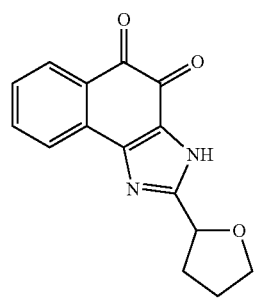
Compound 73
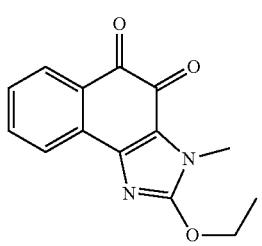
Compound 74
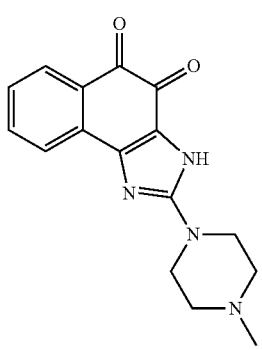
Compound 75
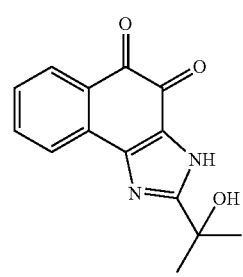
Compound 76
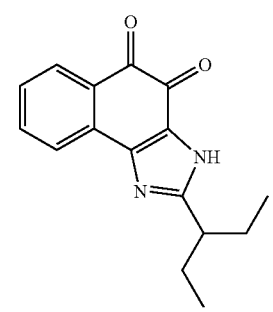
Compound 77
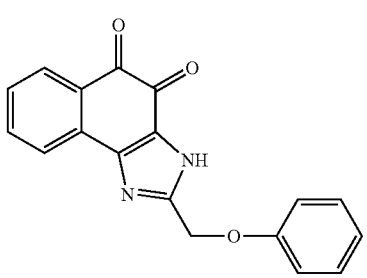
Compound 78
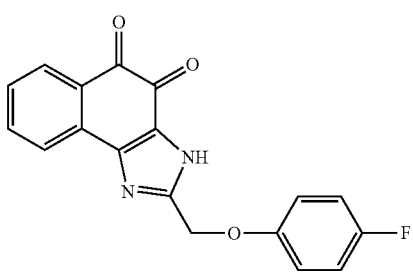
Compound 79
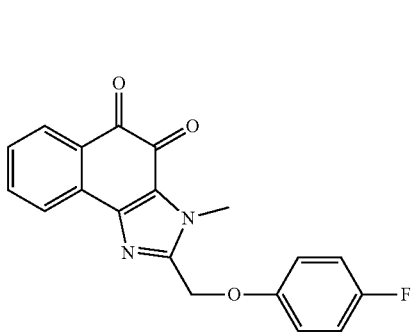
Compound 80
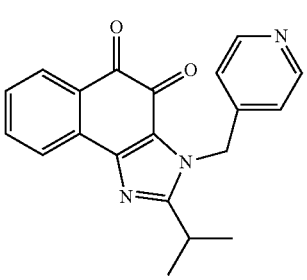

Compound 81
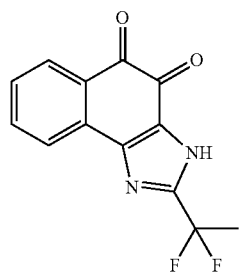
Compound 82
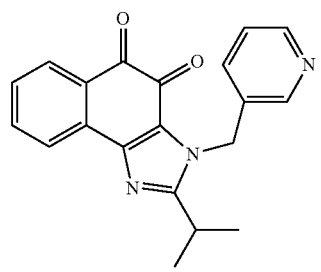
Compound 83
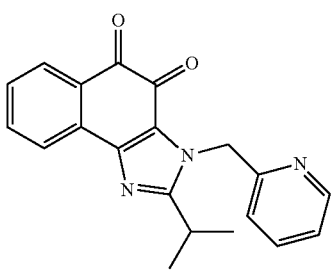
Compound 84
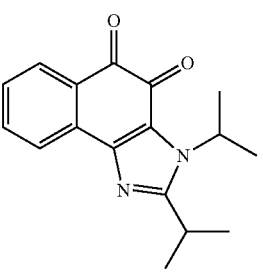
Compound 85
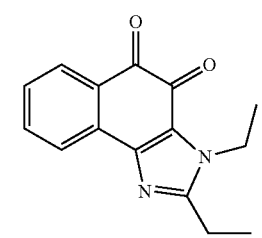
Compound 86
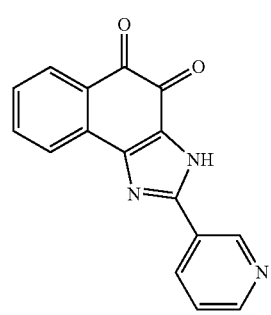
Compound 87
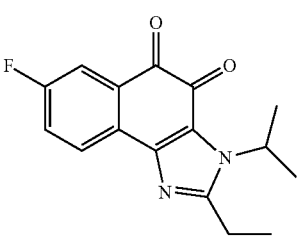
Compound 88
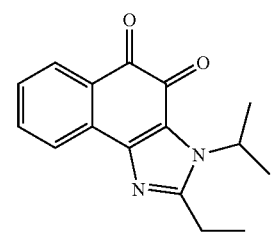
Compound 89
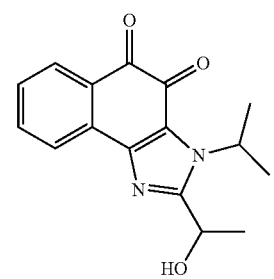
Compound 90
Compound 91
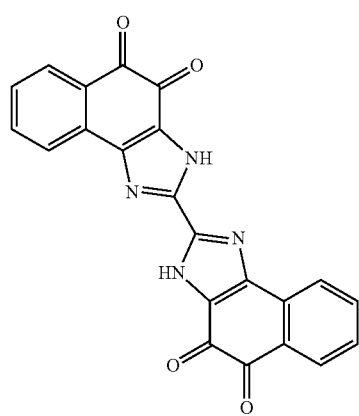

-continued

Compound 92

Compound 93
HCl salt

Compound 94
HCl salt

Compound 95

Compound 96

Compound 97

-continued

Compound 98

Compound 175

Compound 176

Compound 177

Compound 178

Compound 179
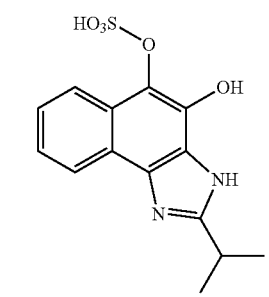
Compound 180
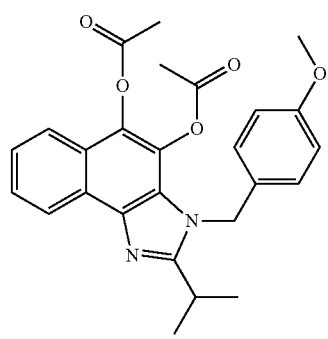
Compound 181
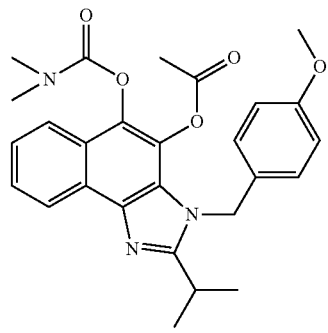
Compound 182
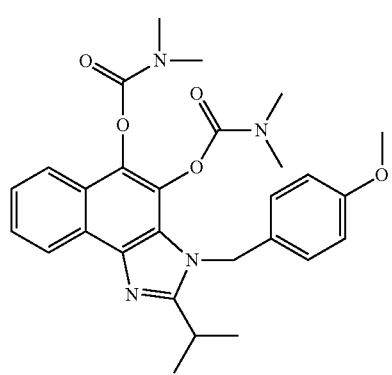
Compound 183
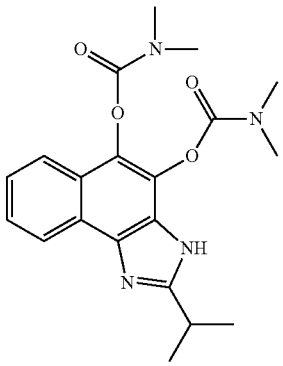
Compound 184
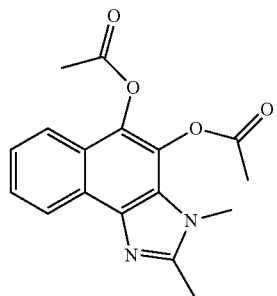
Compound 185
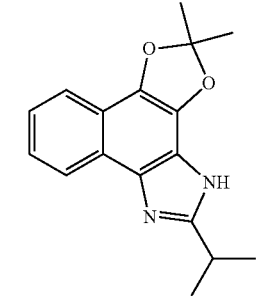
Compound 186
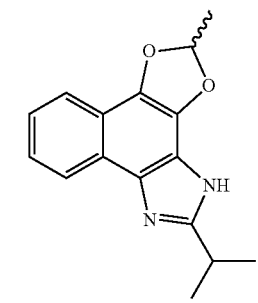
Compound 187
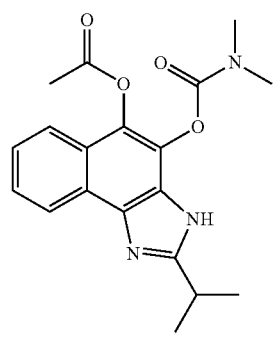

-continued

Compound 188

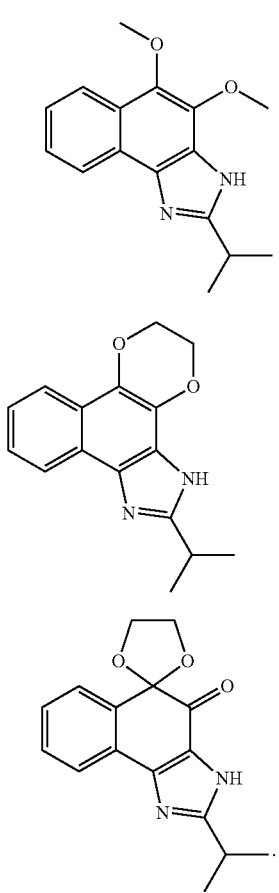

Compound 189

Compound 190

Compound 98

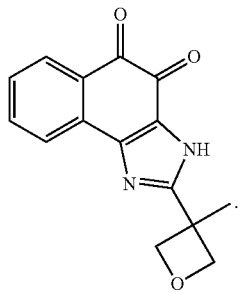

4. The method according to claim 3, wherein the pharmaceutical composition comprises, as an active ingredient, a 1,2-naphthoquinone derivative compound represented by the Chemical Formula 1 or a pharmaceutically acceptable salt thereof, wherein the compound is compound 98 represented below:

5. The method according to claim 1, wherein
the pharmaceutical composition is one formulation selected from the group consisting of powders, granules, tablets, capsules, suspensions, emulsions, syrups, aerosols, epidermal formulations, suppositories, and sterile injection solutions.

6. Compound 98 represented by the following structure, an optical isomer thereof, or a pharmaceutically acceptable salt thereof:

Compound 98

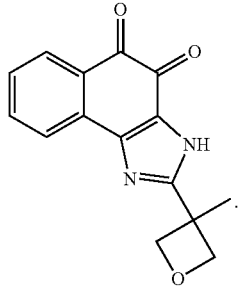

* * * * *